United States Patent [19]
Carpino et al.

[11] Patent Number: 6,100,386
[45] Date of Patent: Aug. 8, 2000

[54] HUMAN GENE/PROTEIN INVOLVED IN CHRONIC MYELOGENOUS LEUKEMIA

[75] Inventors: Nicholas A. Carpino, Memphis, Tenn.; Ryuji Kobayashi, Syosset, N.Y.; David G. Wisniewski, Staten Island, N.Y.; Annabel O'C. Strife; Bayard D. Clarkson, both of New York, N.Y.

[73] Assignees: Cold Spring Harbor Laboratory, Cold Spring Harbor, N.Y.; Sloan-Kettering Institute for Cancer Research, New York, N.Y.

[21] Appl. No.: 08/787,091

[22] Filed: Jan. 22, 1997

Related U.S. Application Data

[60] Provisional application No. 60/030,418, Nov. 1, 1996.

[51] Int. Cl.$^7$ .......................... C07H 21/04; C12N 15/63; C12P 21/00
[52] U.S. Cl. ........................ 536/23.1; 536/22.1; 536/23.5; 435/320.1; 435/325; 435/69.1; 435/71.1
[58] Field of Search .................................. 435/320.1, 325, 435/69.1, 71.1; 536/23.1, 22.1, 23.5

[56] References Cited

FOREIGN PATENT DOCUMENTS

WO 92/20794  11/1992  WIPO .
97/19788  10/1997  WIPO .

OTHER PUBLICATIONS

Database Genbank, subsection EST, Accession No. AA040007, Aug. 1996.
Li et al, J. Virology vol. 67 p. 5402, Sep. 1993.
Database Genbank, subsection EST, Accession No. AA036454, Aug. 1996.
Database Genbank, subsection EST, Accession No. AA082094, Oct. 1996.
Database Genbank, subsection EST, Accession No. H03428, Jun. 1995.
Wisniewski, D. et al., "c–kit Ligand Stimulates Tyrosine Phosphorylation of a Similar Pattern of Phosphotyrosyl Proteins in Primary Primitive Normal Hematopoietic Progenitors That Are Constitutive Phosphorylated in Comparable Primitive Progenitors in Chronic Phage Chronic Myelogenous Leukemia," *Leukemia,* vol. 10:229–237 (1996).
Wang, Lawrence L. et al., "p62 Association with RNA Is Regulated by Tyrosine Phosphorylation," *The Journal of Biological Chemistry,* vol. 270(5):2010–2013 (1995).
Clarkson, B.D. et al., "New Understanding of the Pathogenesis of CML: A Prototype of Early Neoplasia," *Leukemia,* vol. 11:1404–1428 (1997).
Konopka, J., et al., "An alteration of the human c–abl protein in K562 leukemia cells unmasks associated tyrosine kinase activity," *Cell,* 37:1035–1042 (1984).
Wisniewski, D., et al., "A 62–kilodalton tyrosine phosphoprotein constitutively present in primary chronic phase chronic myelogenous leukemia enriched lineage negative blast populations," *Leukemia,* 8:688–693 (1994).
Matsuguchi, T., et al., "Shc phosphorylation in myeloid cells in regulated by GM–CSF, IL3, and SL and is constitutively increased by P210$^{bcr-abl}$," *J. Biol. Chem.,* 269:5016–5021 (1994).
Ellis, C., et al., "Phosphorylation of GAP and GAP–associated proteins by transforming and mitogenic tyrosine kinases," *Nature,* 343:377–381 (1990).
Wong, G., et al., "Molecular cloning and nucleic acid binding properties of the GAP–associated tyrosine phosphoprotein p62, " *Cell,* 69:551–558 (1992).
Marengere, L.E.M. and Pawson , T., "Identification of residues in GTPase–activating protein src homology 2 domains that control binding to tyrosine phosphorylated growth factor receptors and p62," *J. Biol. Chem.,* 267:22779–22786 (1992).
Neet, K. and Hunter, T., "The nonreceptor protein–tyrosine kinase csk complexes directly with the GTPase–activating protein–associated p62 in cells expressing v–src or activated c–src," *Mol. Cell Biol.,* 15:4908–4920 (1995).
Pawson, T., "Protein modules and signaling networks," *Nature,* 373:573–580 (1995).
Trahey, M., and McCormick, F., "A cytoplasmic protein stimulate normal N–ras p21 GTPase, but does not effect oncogenic mutants," *Science,* 238:542–545 (1987).
Valius, M., and Kaslauskas, A., "The GTPase–activating protein of ras suppresses platelet–derived growth factor receptor signaling by silencing phospholipase C–1," *Mol. Cell Biol.,* 15:3058–3071 (1995).
McGlade, J., et al., "The N–terminal region of GAP regulates cytoskeletal structure and cell adhesion," *EMBO J.,* 12:3073–3081 (1993).
Lock, P., et al., "The human p62 cDNA encodes Sam68 and not the rasGAP–associated p62 protein," *Cell,* 84:23–24 (1996).
Moran, M.F., et al., "Protein tyrosine kinases regulate the phosphorylation, protein interactions, subcellular distribution, and activity of p21$^{ras}$ GTPase–activating protein," *Mol. Cell Biol.,* 11:1804–1812 (1991).

(List continued on next page.)

*Primary Examiner*—Julie Burke
*Attorney, Agent, or Firm*—Hamilton, Brook, Smith & Reynolds, P.C.

[57] ABSTRACT

Characteristic of chronic myelogenous leukemia (CML) is the presence of the chimeric p120$^{bcr-abl}$ protein possessing elevated protein tyrosine kinase activity relative to normal c-abl tyrosine kinase. Hematopoietic progenitors isolated from CML patients in the chronic phase contain a constitutively tyrosine phosphorylated protein that migrates at approximately 62 kDa by SDS-PAGE and associates with the p120 ras GTPase-activating protein (GAP). This novel protein, called p62$^{dok}$ (p62 protein downstream of tyrosine kinases), was isolated from a hematopoietic cell line expressing p120$^{bcr-abl}$. Association of p62$^{dok}$ with GAP correlates with its tyrosine phosphorylation. p62$^{dok}$ is rapidly tyrosine phosphorylated upon activation of the c-kit receptor, implicating it as a component of a signal transduction pathway downstream of receptor tyrosine kinases.

7 Claims, 6 Drawing Sheets

OTHER PUBLICATIONS

Lugo, T.G., et al., "Tyrosine kinase activity and transformation potency of bcr–abl oncogene products," *Science* 247:1079–1082. (1990).

Zhao, J.F., et al., "Suppression of RAS and MOS transformation by radicicol," *Oncogene,* 11:161–173 (1995).

Filvaroff, E., et al., "Specific changes of ras GTPase–activating protein (GAP) and a GAP–associated p62 protein during calcium–induced keratinocyte differentiation," *Mol. Cell Biol.,* 12:5319–5328 (1992).

Maa, Ming–Chei et al., "A Protein That Is Highly Related to GTPase–Activiating Protein–Associated p62 Complexes with Phospholipase C$\gamma$," *Mol. Cell. Biol.,* 14(8):5466–5473 (1994).

Ogawa, Wataru et al., "Evidence for Two Distinct 60–Kilodalton Substrates of the SRC Tyrosine Kinase," *J. Biol. Chem.,* 269(47):29602–29608 (1994).

Hosomi, Yoichi et al., "Characterization of a 60–Kilodalton substrate of the Insulin Receptor Kinase," *J. Biol. Chem.,* 269(15):11498–11502 (1994).

Skorski, Tomasz et al., "Negative Regulation of p120GAP GTPase Promoting Activity by p210$^{bcr/abl}$: Implication for RAS–dependent Philadelphia Chromosome Positive Cell Growth," *J. Exp. Med.* 179:1855–1865 (1994).

Carpino, Nick et al., "p62$^{dok}$; A Constitutively Tyrosine–Phosphorylated, GAP–Associated Protein in Chromic Myelogenous Leukemia Progenitor Cells," *Cell* 88:197–204 (1997).

Yamanashi, Yuji and Baltimore, David, "Identification of the Abl–and rasGAP–Associated 62 kDa Protein as a Docking Protein, Dok," *Cell* 88:205–211 (1997).

```
ATGGACGGAGCAGTGATGGAAGGGCCGCTTTTTTTGCAGAGTCAGCGC
TTTGGGACCAAGAGGTGGAGGAAGACCTGGGCCGTGCTCTACCCGGCC
AGTCCCCACGGCGTAGCGCGGCTCGAGTTCTTTGACCATAAGGGGTCG
AGCTCTGGGGGTGGCCGAGGGAGCTCGCGCCGCCTGGACTGCAAAGTG
ATCCGTCTGGCTGAGTGTGTGAGTGTGGCCCCCGTCACCGTGGAGACC
CCCCCTGAGCCCGGCGCCACTGCCTTCCGCCTGGACACTGCTCAGCGC
TCGCACCTGCTGGCGGCCGACGCGCCGTCCAGTGCAGCCTGGGTGCAG
ACGCTGTGCCGAAACGCCTTTCCGAAAGGCAGCTGGACTCTGGCGCCT
ACCGATAACCCACCTAAGCTTTCTGCCCTGGAGATGCTGGAGAACTCC
TTGTACAGCCCTACCTGGGAAGGATCCCAATTCTGGGTAACGGTGCAG
AGGACTGAGGCCGCCGAGCGCTGTGGCCTGCATGGCTCCTACGTGCTG
AGGGTGGAGGCTGAAAGGCTGACTCTCCTGACCGTGGGGCCCAGAGT
CAGATACTGGAGCCACTCCTGTCCTGGCCCTACACTCTGTTGCGTCGC
TATGGCCGGGACAAGGTCATGTTCTCTTTCGAGGCCGGCCGCCGCTGC
CCCTCAGGCCCTGGAACCTTCACCTTCCAGACGGCACAGGGAAATGAC
ATCTTCCAGGCAGTTGAGACTGCCATCCACCGGCAGAAGGCCCAGGGA
AAGGCCGGACAGGGGCACGATGTTCTCAGAGCTGACTCCCATGAAGGG
GAGGTGGCAGAGGGGAAGTTGCCTTCCCCACCTGGCCCCAAGAGCTC
CTCGACAGTCCCCCAGCCCTGTATGCTGAGCCCTTAGACTCCCTGCGC
ATTGCTCCATGCCCTTCCCAGGACTCCCTATACTCAGACCCCTTGGAC
AGCACGTCTGCTCAGGCAGGAGAGGGAGTACAACGGAAGAAACCTCTC
TATTGGGACTTGTATGAGCATGCGCAGCAGCAGTTGCTGAAGGCCAAG
CTGACAGACCCCAAAGAGGATCCCATCTATGATGAACCTGAGGGCCTG
GCCCCAGTCCCTCCCCAGGGCCTTTATGATCTGCCTCGGGAGCCCAAG
GATGCATGGTGGTGCCAAGCTCGGGTGAAGGAGGAGGGCTATGAGCTC
CCCTACAACCCTGCCACTGATGACTACGCTGTGCCACCCCTCGGAGC
ACAAAGCCCCTCCTTGCTCCCAAGCCCCAGGGCCCAGCCTTCCCTGAA
CCTGGTACTGCAACTGGCAGTGGCATCAAAAGCCACAACTCAGCCCTG
TACAGCCAGGTCCAGAAGAGCGGGGCCTCAGGGAGCTGGGACTGTGGG
CTCTCTAGAGTAGGGACTGACAAGACTGGGGTCAAGTCAGAGGGCTCT
ACCTGA
```

FIGURE 2A

```
Met Asp Gly Ala Val Met Glu Gly Pro Leu Phe Leu Gln Ser Gln Arg
Phe Gly Thr Lys Arg Trp Arg Lys Thr Trp Ala Val Leu Tyr Pro Ala
Ser Pro His Gly Val Ala Arg Leu Glu Phe Phe Asp His Lys Gly Ser
Ser Ser Gly Gly Gly Arg Gly Ser Ser Arg Arg Leu Asp Cys Lys Val
Ile Arg Leu Ala Glu Cys Val Ser Val Ala Pro Val Thr Val Glu Thr
Pro Pro Glu Pro Gly Ala Thr Ala Phe Arg Leu Asp Thr Ala Gln Arg
Ser His Leu Leu Ala Ala Asp Ala Pro Ser Ser Ala Ala Trp Val Gln
Thr Leu Cys Arg Asn Ala Phe Pro Lys Gly Ser Trp Thr Leu Ala Pro
Thr Asp Asn Pro Pro Lys Leu Ser Ala Leu Glu Met Leu Glu Asn Ser
Leu Tyr Ser Pro Thr Trp Glu Gly Ser Gln Phe Trp Val Thr Val Gln
Arg Thr Glu Ala Ala Glu Arg Cys Gly Leu His Gly Ser Tyr Val Leu
Arg Val Glu Ala Glu Arg Leu Thr Leu Leu Thr Val Gly Ala Gln Ser
Gln Ile Leu Glu Pro Leu Leu Ser Trp Pro Tyr Thr Leu Leu Arg Arg
Tyr Gly Arg Asp Lys Val Met Phe Ser Phe Glu Ala Gly Arg Arg Cys
Pro Ser Gly Pro Gly Thr Phe Thr Phe Gln Thr Ala Gln Gly Asn Asp
Ile Phe Gln Ala Val Glu Thr Ala Ile His Arg Gln Lys Ala Gln Gly
Lys Ala Gly Gln Gly His Asp Val Leu Arg Ala Asp Ser His Glu Gly
Glu Val Ala Glu Gly Lys Leu Pro Ser Pro Pro Gly Pro Gln Glu Leu
Leu Asp Ser Pro Pro Ala Leu Tyr Ala Glu Pro Leu Asp Ser Leu Arg
Ile Ala Pro Cys Pro Ser Gln Asp Ser Leu Tyr Ser Asp Pro Leu Asp
Ser Thr Ser Ala Gln Ala Gly Glu Gly Val Gln Arg Lys Lys Pro Leu
Tyr Trp Asp Leu Tyr Glu His Ala Gln Gln Gln Leu Leu Lys Ala Lys
Leu Thr Asp Pro Lys Glu Asp Pro Ile Tyr Asp Glu Pro Glu Gly Leu
Ala Pro Val Pro Pro Gln Gly Leu Tyr Asp Leu Pro Arg Glu Pro Lys
Asp Ala Trp Trp Cys Gln Ala Arg Val Lys Glu Glu Gly Tyr Glu Leu
Pro Tyr Asn Pro Ala Thr Asp Asp Tyr Ala Val Pro Pro Pro Arg Ser
Thr Lys Pro Leu Leu Ala Pro Lys Pro Gln Gly Pro Ala Phe Pro Glu
```

FIGURE 2B

Pro Gly Thr Ala Thr Gly Ser Gly Ile Lys Ser His Asn Ser Ala Leu
Tyr Ser Gln Val Gln Lys Ser Gly Ala Ser Gly Ser Trp Asp Cys Gly
Leu Ser Arg Val Gly Thr Asp Lys Thr Gly Val Lys Ser Glu Gly Ser
Thr

FIGURE 2C p62$^{dok}$ Peptide Sequencing Results

| Peptide | Sequence |
|---|---|
| K12 | QG (H) DVLRAD |
| K15 | PQGPAFPEPGTATGS |
| K16 | S (G) TLAPTD / NN |
| K19 | GQGHDVLRADSHEG (E) VA |
| K29 | WAVLYPASPHGVARLEFFDHK |
| K31 | PLY?DLYEHAQQQLLK |
| K60 | MFSFEAGRR?PSGPGTFTFQ TAQGNDIFQAVETAI (H) RQ |

FIGURE 3

PCR Primers

Schematic Design:

```
            K29N2 ─────────────►
    K29N1 ─────────────►  K29N3 ─────────────►
```
K29:  WAVLYPASPHGVARLEFFDHK

K31:  PLY?DLYEHAQQQLLK
```
                       ◄───────── K31C1
                   ◄───────────── K31C2
               ◄───────────────── K31C3
```

Primer Sequence:

K29N1: 5' TGGGCIGTIT/CTITAT/CCC 3'

K29N2: 5' GTIT/CTITAT/CCCT/AGCIT/AC/GCCICATGG 3'

K29N3: 5' CATGGIGTIGCIA/CGIT/CTIGAA/GTT 3'

K31C1: 5' TTIAG/AIAG/AIAG/AT/CT/CTGT/CTGT/CTGA/G/C/TGC 3'

K31C2: 5' T/CTGT/CTGT/CTGIGCATGT/CTCA/GTA 3'

K31C3: 5' T/CTGIGCATGT/CTCA/GTAIAG/AA/GTC 3'

FIGURE 4

HUMAN GENE/PROTEIN INVOLVED IN CHRONIC MYELOGENOUS LEUKEMIA

RELATED APPLICATIONS

This application claims priority to U.S. Provisional Application Ser. No. 60/030,418, filed Nov. 1, 1996, the teachings of which are expressly incorporated herein by reference.

GOVERNMENT FUNDING

This invention was made, in whole or in part, with support under National Institutes of Health/National Cancer Institute Grant No. 5P01 CA64593-03. The U.S. Government has certain rights in the invention.

BACKGROUND OF THE INVENTION

Chronic myelogenous leukemia (CML) is a disease having clinical and pathological features distinct from those of other forms of leukemia. It is widely accepted that the cause of CML is a specific chromosomal translocation between human chromosome 9 and human chromosome 22. The N chromosome resulting from this translocation is commonly referred to as the Philadelphia chromosome. Darnell, J. et al., *Molecular Cell Biology*, 2nd Ed., W. H. Freeman and Co., New York (1990), p. 992. The gene for c-abl (ABL), a tyrosine kinase thought to be involved in growth control, resides on the distal arm of human chromosome 9, while the gene for c-bcr (BCR) resides on human chromosome 22. The translocation places the promoter distal three exons of ABL, including those elements which encode the tyrosine kinase domain, downstream of either the first or second exon of BCR. Chung, S. and Wong, P. M. C., *Oncogene*, 10:1261–1268 (1995). The product of the translocation between human chromosome 9 and human chromosome 22 is a chimeric gene, BCR-ABL, which encodes a fusion protein, often referred to as $p185^{bcr-abl}$ or $p210^{bcr-abl}$, depending upon the inclusion of the second exon of BCR. Bartram, C. R., et al., *Nature*, 306:277–280 (1983). $p185^{bcr-abl}$ causes acute leukemia, typically lymphoblastic; $p210^{bcr-abl}$ usually causes CML, but can occasionally also cause acute leukemia.

Compared to normal c-abl, bcr-abl has increased tyrosine kinase activity. Konopka, J., et al., *Cell*, 37:1035–1042 (1984). Additionally, c-abl, as a non-receptor tyrosine kinase, functions both in the nucleus and the cytoplasm and bcr-abl functions exclusively in the cytoplasm. These two characteristics of bcr-abl are essential elements of its transforming abilities. McWhirter, J. R., et al., *Mol. Cell Bio.*, 11:1553–1565 (1991).

Following this chromosomal translocation within a single, primitive myeloid stem cell, the progeny of the affected cell gradually populate the entire intermediate and late hematopoietic maturational compartments. Despite the presence of the Philadelphia chromosome, these progeny, referred to as Ph⁺ cells, are able to differentiate and mature along the various myeloid lineages while retaining the capacity to function as their normal, unaffected counterparts. Invariably, in an average span of three to five years, the disease progresses into a malignant stage known as blast crisis. The affected cells acquire additional chromosomal abnormalities and lose their ability to differentiate and mature, resulting in the functional breakdown of the hematopoietic system. Clarkson, B. and Strife, A., *Leukemia*, 7:1683–1721 (1993). Daley, G. Q. and Ben Neriah, Y., *Adv. Cancer Res.*, 57:151–184 (1991). Deisseroth, A. B. and Arlinghaus, R. B., eds. *Chronic Myelogenous Leukemia-Molecular Approaches to Research and Therapy*, New York, Marcel Dekker (1991). Sawyers, C. L. et al., *Cell*, 64:337–350 (1991).

Clinical treatment of CML has remained essentially unchanged for many years. To date, with the exception of marrow ablative chemotherapy and/or total body irradiation followed by allogeneic bone marrow transplantation, no effective cure has been developed for the disease. Only a minority of CML patients have been cured by complete bone marrow transplantation. Treatment with alpha interferon has led to durable remissions in about 10–20% of chronic phase patients, but longer follow-ups are necessary to determine if these patients will have late relapses. In light of this, the need for better treatment methods is apparent.

SUMMARY OF THE INVENTION

As described herein, Applicants have identified and characterized a protein which is constitutively tyrosine phosphorylated in mammalian, such as human, cells in which an oncogenic tyrosine kinase is active. This protein, referred to as p62 protein downstream of tyrosine kinases, or $p62^{dok}$, is tyrosine phosphorylated in hematopoietic cells, or cells which are progeny thereof, after stimulation with a ligand for a receptor tyrosine kinase and, in its tyrosine phosphorylated form, but not in its non-tyrosine phosphorylated form, binds p120 ras GTPase-activating protein (GAP). This protein has also been referred to (e.g. in U.S. Provisional Application Ser. No. 60/030,418, filed Nov. 1, 1996) as GAT62. The terms $p62^{dok}$ and GAT62 can be used interchangeably to refer to the same protein. The $p62^{dok}$ protein is involved in a signal transduction pathway initiated by a receptor tyrosine kinase and is rapidly tyrosine phosphorylated after the receptor tyrosine kinase is activated. The $p62^{dok}$ protein of the present invention is the 62 kDa GAP-associating protein which is constitutively tyrosine phosphorylated in hematopoietic cells, or cells which are progeny thereof, of individuals with CML.

The $p62^{dok}$ protein of the present invention is present in normal cells (cells in which an oncogenic tyrosine kinase is not present or is inactive) and, in one embodiment comprises the amino acid sequence of SEQ ID NO.: 2. In a further embodiment, $p62^{dok}$ protein of the present invention is encoded by DNA which hybridizes, as described herein, to DNA comprising the nucleotide sequence of SEQ ID NO.: 1. $p62^{dok}$ protein obtained from normal hematopoietic cells, or cells which are progeny thereof, is not constitutively tyrosine phosphorylated. In normal cells, $p62^{dok}$ protein may be tyrosine phosphorylated in the absence of an oncogenic tyrosine kinase in normal cells. However, in normal cells, it will not be in a state of constitutive (constant) phosphorylation. Alternatively, $p62^{dok}$ protein may exist in a non-tyrosine phosphorylated state in the absence of an oncogenic tyrosine kinase in normal cells. Non-tyrosine phosphorylated $p62^{dok}$ protein does not bind GAP; tyrosine phosphorylated $p62^{dok}$ protein, regardless of whether the phosphorylation is constitutive, binds GAP. In normal cells, stimulation of specific cell surface receptors results in tyrosine phosphorylation of $p62^{dok}$ protein. Tyrosine phosphorylation in the absence of an oncogenic tyrosine kinase in normal cells is referred to herein as normal tyrosine phosphorylation. The resulting $p62^{dok}$ protein is referred to as normal or wild type tyrosine phosphorylated $p62^{dok}$. In contrast, $p62^{dok}$ protein obtained from cells, such as human hematopoietic progenitor cells, in which tyrosine kinase activity is altered (e.g., as to level, timing, cellular location) is constitutively tyrosine phosphorylated. This is referred to herein as aberrant or constitutive tyrosine phosphorylation.

The resulting p62$^{dok}$ protein is referred to as aberrantly or constitutively tyrosine phosphorylated p62$^{dok}$. As described herein, p62$^{dok}$ protein is present in hematopoietic progenitor cells, or cells which are progeny thereof, from CML patients in which a chimeric bcr-abl gene is expressed and the protein is constitutively tyrosine phosphorylated.

Constitutively tyrosine phosphorylated p62$^{dok}$ protein purified from a hematopoietic cell line expressing an oncogenic tyrosine kinase is also the subject of this invention. One embodiment of such a protein is constitutively tyrosine phosphorylated p62$^{dok}$ protein, isolated from Mo7/p210 cells and which binds GAP. The two components of this doublet have molecular weights of approximately 62 and 64 kDa (based on migration by SDS-PAGE). The present invention also relates to p62$^{dok}$ protein, purified from a hematopoietic cell line lacking an oncogenic tyrosine kinase or containing an inactive oncogenic tyrosine kinase, which exhibits normal tyrosine phosphorylation. One embodiment of such a protein is normal tyrosine phosphorylated p62$^{dok}$ protein, isolated from Mo7 cells, which migrates as a singlet with a molecular weight of approximately 61 kDa (based on migration by SDS-PAGE) and does not bind p120 ras GAP.

The present invention also relates to isolated nucleic acids (DNA, RNA), referred to as p62$^{dok}$-encoding nucleic acids, which encode p62$^{dok}$ protein, or fragments or portions thereof, as described herein. The term Dok is used to refer to the gene encoding the complete p62$^{dok}$ protein.

In one embodiment, the p62$^{dok}$-encoding nucleic acid of the present invention is DNA which comprises the nucleic acid sequence of SEQ ID NO:1. In another embodiment, p62$^{dok}$-encoding nucleic acid is DNA which hybridizes under highly stringent conditions with a nucleic acid having the nucleotide sequence of SEQ ID NO:1 and which encodes a protein which is involved in a signal transduction pathway initiated by a receptor tyrosine kinase, such as a pathway initiated by a receptor tyrosine kinase which also initiates a pathway in which p62$^{dok}$ protein encoded by SEQ ID NO.: 1 participates. In a further embodiment, the p62$^{dok}$-encoding nucleic acid of the present invention is DNA, which due to the degeneracy of the genetic code, encodes the amino acid sequence encoded by DNA having the nucleotide sequence of SEQ ID NO.: 1. The present invention also relates to mRNA encoded by (transcribed from) p62$^{dok}$-encoding DNA.

The present invention also relates to nucleic acids, useful as probes and primers, which comprise p62$^{dok}$-encoding DNA or fragments or portions of DNA encoding p62$^{dok}$ (e.g., portions of SEQ ID NO.: 1). The probes and primers are useful in identifying, isolating and/or amplifying p62$^{dok}$-encoding DNA (e.g., for diagnostic, prognostic, or research purposes). For example, the probes are useful to identify cells which contain p62$^{dok}$-encoding DNA and, thus, to diagnose a condition in which an oncogenic tyrosine kinase is active, such as in CML, to assess the likelihood that an individual will develop the condition (e.g., CML) and to monitor the progression of the condition in an individual. Portions of DNA encoding p62$^{dok}$ are also useful as primers, e.g., in amplification methods.

The present invention also relates to host cells which contain p62$^{dok}$-encoding nucleic acid (DNA, RNA) and express the p62$^{dok}$ protein. The host cell may, optionally, express an oncogenic tyrosine kinase at levels which are elevated, the same as or decreased, relative to activity of a normal (non-oncogenic) tyrosine kinase. In a particular embodiment, the host cell comprises nucleic acid encoding the p62$^{dok}$ protein of the present invention operably linked to an expression control sequence; the encoded p62$^{dok}$ protein is expressed when the host cell is maintained under conditions suitable for expression.

The present invention also relates to antibodies or functional portions thereof (e.g., an antigen binding portion such as an Fv, Fab, Fab', or F(ab')$_2$ fragment) which bind the p62$^{dok}$ protein of the present invention. In one embodiment, antibodies of the present invention recognize (bind) aberrantly tyrosine phosphorylated p62$^{dok}$, but do not recognize (bind) normal tyrosine phosphorylated p62$^{dok}$. Such antibodies are useful, for example, in detecting or identifying cells which contain aberrantly tyrosine phosphorylated p62$^{dok}$ and, thus, for detecting or identifying cells in which an oncogenic tyrosine kinase is active. Tyrosine phosphorylation of p62$^{dok}$ occurs in cells, such as chronic phase hematopoietic progenitor cells from CML patients. Therefore, tyrosine phosphorylated p62$^{dok}$ can be detected and, optionally, quantitated, to diagnose or aid in the diagnosis of CML and to monitor-its progression.

The present invention also relates to a method of detecting p62$^{dok}$ protein, particularly aberrantly tyrosine phosphorylated p62$^{dok}$ protein, in a sample of cells, such as cancer cells or cells thought to be progressing toward a cancerous state. As described herein, the appearance of aberrantly tyrosine phosphorylated p62$^{dok}$ in cells, such as hematopoietic progenitor cells, is correlated with progression toward the transformed phenotype. Thus, it is possible to assess progression of cells toward transformation by, for example, quantitative or qualitative assessment of phosphorylation of p62$^{dok}$. Increased tyrosine phosphorylated p62$^{dok}$ (relative to the amount of tyrosine phosphorylated p62$^{dok}$ present in normal cells) is indicative of unregulated or increased tyrosine kinase activity and, thus, assessment of tyrosine phosphorylated p62$^{dok}$ provides a method of diagnosing, aiding in the diagnosis of and monitoring the progression of diseases, particularly CML and other human cancers, in which aberrant (e.g., unregulated or increased) tyrosine kinase activity plays a causative role. Alternatively, presence of tyrosine phosphorylated p62$^{dok}$ at a different time in the cell cycle from that at which normal tyrosine phosphorylation of p62$^{dok}$ occurs can also be assessed in diagnosing, aiding in the diagnosis of or monitoring the progression of a condition (e.g. cancer in which tyrosine kinase activity plays a causative role).

In one embodiment of the present method of detecting a tyrosine phosphorylated p62$^{dok}$ protein, a sample of cells to be assessed (e.g., cells obtained from an individual, such as a human) is combined with an agent, such as an antibody or a small organic molecule, which recognizes (binds) aberrantly tyrosine phosphorylated p62$^{dok}$, but not normal tyrosine phosphorylated p62$^{dok}$ Binding of the agent is assessed, using known methods. If binding occurs (e.g., if a complex of the agent and aberrantly tyrosine phosphorylated p62$^{dok}$ is formed), then aberrantly tyrosine phosphorylated p62$^{dok}$ is present, indicating that the cell is progressing toward or has acquired the transformed phenotype. Alternatively, an antibody or other agent which binds both normal and aberrantly tyrosine phosphorylated p62$^{dok}$ is used and the extent and/or timing of tyrosine phosphorylation of p62$^{dok}$ is assessed in the cells being analyzed and compared with the extent and/or timing of p62$^{dok}$ tyrosine phosphorylation in control cells (e.g., corresponding normal cells). Abnormal tyrosine phosphorylation in the cells being analyzed, as indicated, for example, by tyrosine phosphorylation of p62$^{dok}$ to a greater extent, at a different point in the life cycle of the cells or at different tyrosine residue(s) than occurs in the normal cells, indicates that the cells being assessed are progressing toward or have acquired the transformed phenotype.

In one embodiment of the present method, an antibody which binds aberrantly tyrosine phosphorylated p62$^{dok}$ but does not bind the normal tyrosine phosphorylated p62$^{dok}$, is combined with cells to be assessed, under conditions suitable for specific binding of the antibody to the aberrantly tyrosine phosphorylated p62$^{dok}$ protein. The presence of antibody-aberrantly-tyrosine phosphorylated p62$^{dok}$ protein complex is assessed, such as by detecting a label present on the antibody in the complex or by addition of an antibody which binds the antibody specific for aberrantly tyrosine phosphorylated p62$^{dok}$. Presence of the complex indicates that aberrantly tyrosine phosphorylated p62$^{dok}$ is present and, thus, that the cell is progressing toward or has acquired the transformed phenotype.

The present method of detecting aberrantly tyrosine phosphorylated p62$^{dok}$ in cells also provides a method of assessing the progression of CML or other types of cancer in which p62$^{dok}$ is constitutively tyrosine phosphorylated and, thus, enables a method of providing a prognosis of the cancer.

In one embodiment, cells which contain an oncogenic tyrosine kinase, which aberrantly phosphorylates a protein which, in its phosphorylated form, forms a complex with p120 ras GAP, progress to a transformed phenotype. A sample of cells to be assessed is obtained from the individual. This sample is treated to render aberrantly tyrosine phosphorylated p62$^{dok}$ available for binding by antibodies which bind aberrantly tyrosine phosphorylated p62$^{dok}$ but do not bind normal tyrosine phosphorylated p62$^{dok}$, thereby producing a treated sample. The treated sample is combined with antibodies which bind aberrantly tyrosine phosphorylated p62$^{dok}$ but do not bind normal tyrosine phosphorylated p62$^{dok}$, under conditions appropriate for binding of the antibodies to aberrantly tyrosine phosphorylated p62$^{dok}$. The extent to which the antibody binds aberrantly tyrosine phosphorylated p62$^{dok}$ is determined, wherein if binding of the antibody with aberrantly tyrosine phosphorylated p62$^{dok}$ occurs, the sample contains transformed cells or cells progressing to the transformed phenotype. The aforementioned steps are repeated at intervals, thereby producing sequential determinations of the extent to which the antibody binds aberrantly tyrosine phosphorylated p62$^{dok}$ Finally, the sequential determinations of the extent to which the antibody binds aberrantly tyrosine phosphorylated p62$^{dok}$ are determined wherein if the extent determined at an interval is greater than the extent determined at the previous interval, the condition is progressing and if the extent determined at an interval is less than the extent determined at the previous interval, the condition is not progressing.

Further, the present invention relates to methods of therapy for CML and other types of cancers and other conditions in which an oncogenic tyrosine kinase acts to constitutively tyrosine phosphorylate p62$^{dok}$ protein. In the present method, a drug which interferes with tyrosine phosphorylation of p62$^{dok}$ and/or tyrosine phosphorylated p62$^{dok}$ function, directly or indirectly, is introduced into cells in which p62$^{dok}$ is undergoing constitutive tyrosine phosphorylation or has been constitutively tyrosine phosphorylated. In the method, the drug can be an antibody (e.g., an antibody which selectively binds tyrosine phosphorylated p62$^{dok}$), a nucleic acid (e.g., antisense DNA, DNA or RNA encoding a protein which degrades or otherwise disables tyrosine phosphorylated p62$^{dok}$ or a protein or peptide which mimics p120 ras GAP by binding tyrosine phosphorylated p62$^{dok}$), the GAP "mimic" itself, or a small organic molecule. The drug is introduced into an individual, such as a human or other mammal, in need of therapy (prevention, slowing or inhibition of progression toward or reversal of the transformed phenotype) for CML or other cancer in which an oncogenic tyrosine kinase which constitutively tyrosine phosphorylated p62$^{dok}$ is present. The drug can be administered systemically (e.g., orally, intramuscularly, intravenously, rectally) or introduced into a specific site (e.g., into bone marrow or a tumor) by known methods (e.g., injection, microparticle projectile bombardment). An antibody which selectively binds tyrosine phosphorylated p62$^{dok}$ will prevent its further function, such as by preventing it from binding p120 ras GAP. Antisense DNA will bind DNA encoding p62$^{dok}$ and prevent expression of p62$^{dok}$. DNA encoding a protein which degrades or otherwise disables tyrosine phosphorylated p62$^{dok}$ and DNA encoding a GAP "mimic" will be expressed in cells and the resulting product will act to inhibit p62$^{dok}$. Similarly, a protein or peptide which mimics GAP will interfere with p62$^{dok}$ function by binding p62$^{dok}$ and preventing it from forming a complex with GAP and/or interacting with other molecule(s) with which it would otherwise interact.

In another embodiment, a transgenic, non-human vertebrate, such as a transgenic, non-human mammal, in which cells have been modified to express, or modified to be able to express upon induction, an oncogenic tyrosine kinase is used as a model for the study of CML. For instance, the animal may be used to identify drugs useful in treating or preventing CML. In another example, a transgenic animal, which has restricted expression of the Dok gene in hematopoietic cells, could be used to study BCR-ABL signaling. In another example, a transgenic animal, in which expression of the Dok gene is reduced or eliminated (e.g., by removal or disablement of the gene), may be used to study the ability of BCR-ABL to transform hematopoietic cells.

BRIEF DESCRIPTION OF THE DRAWINGS

FIGS. 2A–2C shows the nucleotide sequence (SEQ ID NO.: 1) and amino acid sequence (SEQ ID NO.: 2) of human p62$^{dok}$ cDNA.

FIG. 3 shows amino acid sequences (SEQ ID NO.: 3–9) of individual peptides purified by HPLC. Residues which were unreadable are indicated with a '?,' and those whose identity was uncertain are marked with parentheses.

FIG. 4 shows the design of successful oligonucleotide primers, which were designed based on the amino acid sequence of the indicated peptides (SEQ ID NO.: 7–8) and were degenerate at the indicated positions. Inosine bases (I) were included at positions of greatest degeneracy in the nucleotide sequence SEQ ID No.: 10–15.

DETAILED DESCRIPTION OF THE INVENTION

Figure 1:
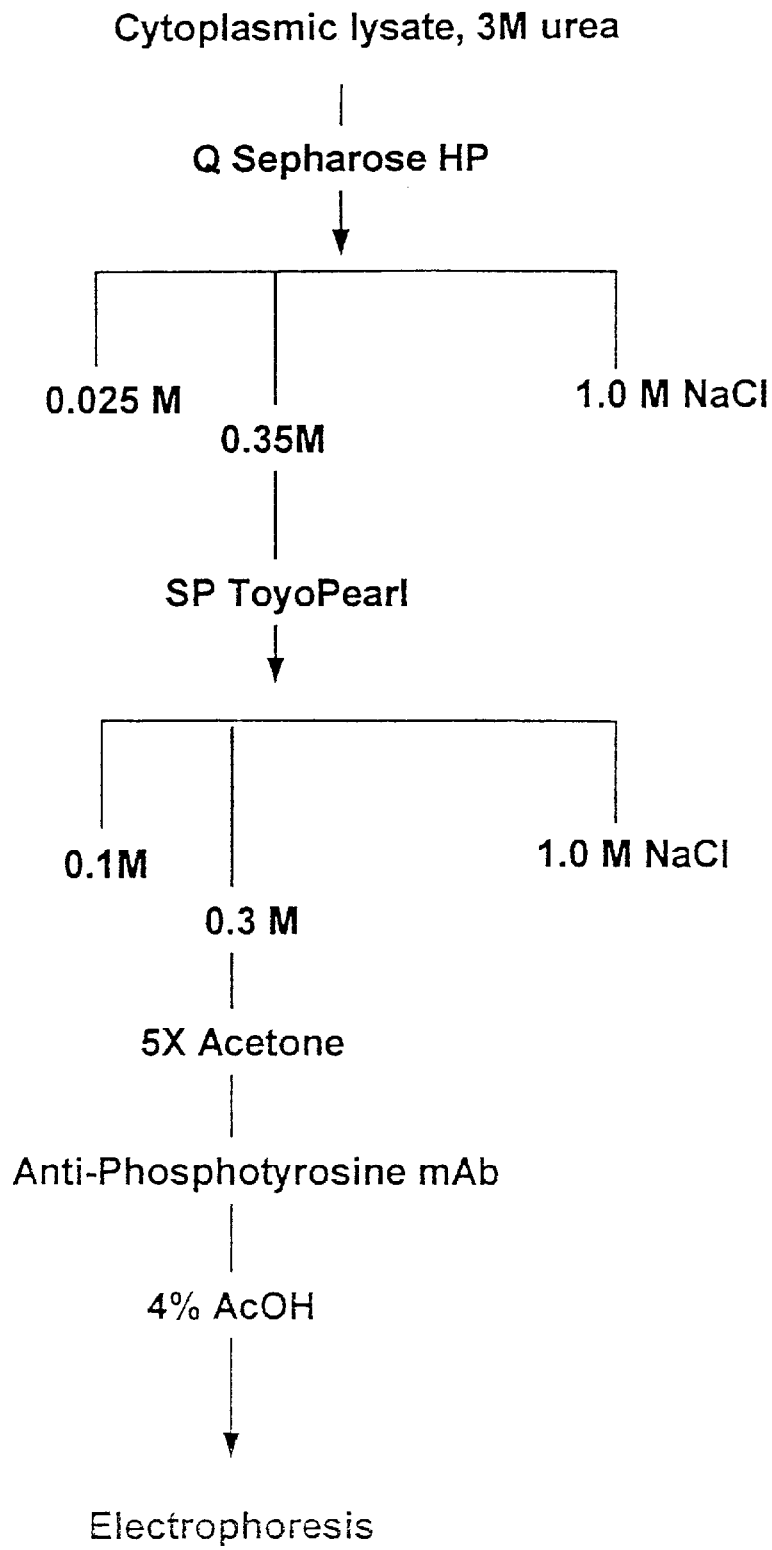
FIG. 1 shows a scheme for p62$^{dok}$ purification, in which cytoplasmic lysate of Mo7/p210 cells is passed sequentially over two ion exchange columns and subsequently α-phosphotyrosine immuno-affinity chromatography is used to capture tyrosine phosphorylated p62$^{dok}$.

The present invention relates to isolated nucleic acids (DNA, RNA) referred to as p62-encoding nucleic acids and portions or fragments of p62-encoding nucleic acids, such as fragments of SEQ ID NO.: 1, which do not encode p62$^{dok}$. Such fragments are useful as nucleic acid probes for use in hybridization assays and as primers for use, e.g., in amplification reactions. The present invention also relates to isolated p62$^{dok}$ proteins and polypeptides, as well as to methods for obtaining isolated p62$^{dok}$ proteins and polypeptides (normal and aberrantly phosphorylated p62$^{dok}$) and for producing recombinant p62$^{dok}$ proteins in cells in which tyrosine kinase activity is altered, resulting in aberrant tyrosine phosphorylation of cellular proteins. The present invention also relates to antibodies which bind p62$^{dok}$ proteins and polypeptides, methods of detecting p62$^{dok}$ in cells, and methods of therapy for CML and other types of cancer and other conditions in which an oncogenic tyrosine kinase aberrantly tyrosine phosphorylates a cellular protein, such as p62$^{dok}$. Following is a description of the compositions and methods of the present invention.

Nucleic Acids, Constructs and Vectors

As described herein, Applicants have isolated and sequenced DNA, referred to as p62$^{dok}$-encoding DNA, from a human teratocarcinoma cDNA library and have shown that it encodes a protein (p62$^{dok}$) which is constitutively tyrosine phosphorylated in mammalian, specifically human, cells in which tyrosine kinase activity is altered.

p62$^{dok}$-encoding DNA, as defined herein, includes: a) DNA comprising the nucleotide sequence of, or a nucleotide sequence substantially the same as, SEQ ID NO.: 1 or a portion of SEQ ID NO.: 1 sufficient to encode functional p62$^{dok}$ protein (e.g., a portion comprising the open reading frame); b) DNA which hybridizes to DNA of a) and encodes p62$^{dok}$; c) DNA which encodes the amino acid sequence of SEQ ID NO.: 2 or a sufficient number of amino acid residues of SEQ ID NO.: 2 for the encoded protein to be a functional p62$^{dok}$ protein; d) DNA which, due to the degeneracy of the genetic code, encodes the amino acid sequence encoded by DNA having the nucleotide sequence of SEQ ID NO.: 1; and e) complements of a), b), c) or d). p62$^{dok}$-encoding DNA can be genomic DNA or cDNA and can be obtained from sources in which it occurs in nature (e.g., tissue or cell samples), from a DNA library, by means of recombinant technology or amplification procedures, by synthetic techniques. p62$^{dok}$-encoding DNA is mammalian, particularly human, DNA. It is useful to produce p62$^{dok}$ protein or polypeptide, which can be carried out using available expression systems.

Alternatively, DNA of the present invention can be anti-sense DNA. Antisense nucleic acid is complementary, in whole or in part, to a sense strand and can hybridize with the sense strand. The target can be DNA, or its RNA counterpart (i.e., wherein T residues of the DNA are U residues in the RNA counterpart). When introduced into a cell, antisense nucleic acid can inhibit the expression of the gene encoded by the sense strand. Antisense nucleic acids can be produced by standard techniques.

In a particular embodiment, the antisense nucleic acid is wholly or partially complementary to and hybridizes with a nucleic acid having a sequence of the complement of the strand shown in FIG. 1 (SEQ ID NO:1). For example, antisense nucleic acid can be complementary to a target nucleic acid having the sequence shown as the open reading frame in FIG. 1 (SEQ ID NO:1) or to a portion thereof sufficient to allow hybridization. In another embodiment, the antisense nucleic acid is wholly or partially complementary to and hybridizes with a target nucleic acid which encodes p62$^{dok}$ protein.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated.

Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes.

A nucleic acid encoding p62$^{dok}$ protein or a variant (e.g, portion) thereof can be incorporated into a vector, operably linked to one or more expression control elements, and the resulting construct introduced into host cells, which are maintained under conditions suitable for expression of p62$^{dok}$ protein, whereby the encoded protein is produced. The construct can be introduced into cells by a method appropriate to the host cell selected (e.g., transformation, transfection, electroporation, infection). The encoded p62$^{dok}$ protein can be isolated from the host cells or medium. p62$^{dok}$ RNA can be obtained by these means as well.

Fragments of p62$^{dok}$-encoding DNA, such as fragments of DNA of SEQ ID NO.: 1, which do not encode p62$^{dok}$ are useful as probes and primers for assays, amplification procedures, diagnostic and therapeutic methods. For example, p62$^{dok}$ DNA fragments characteristic of p62$^{dok}$-encoding DNA can be used as probes in standard hybridization methods to identify cells which contain p62$^{dok}$-encoding DNA. DNA which encodes p62$^{dok}$ (full-length p62$^{dok}$ DNA) can also be used as a probe.

The nucleic acids can be used as probes to detect and/or isolate (e.g., by hybridization with RNA or DNA) p62$^{dok}$-encoding DNA comprising SEQ ID NO.: 1 or variants, for example, in a sample (e.g., tissue) obtained from a host (e.g. human). Moreover, the presence or frequency of p62$^{dok}$-encoding DNA or a particular variant in a sample(s) obtained from one or more affected hosts, as compared with a sample(s) from normal host(s), can be indicative of an association between a disease and a particular variant, which in turn can be used in the diagnosis of the condition.

DNA fragments are also useful for therapeutic purposes. For example, sense or anti-sense p62$^{dok}$ DNA fragments can be introduced into cells in which p62$^{dok}$ expression is to be reduced (e.g., to decrease progression toward the transformed phenotype, by preventing or reducing expression of p62$^{dok}$ and, thus, reducing its availability for tyrosine phosphorylation). The sense or anti-sense p62$^{dok}$ DNA fragments hybridize with their complements, rendering them unavailable for further processing in the cells; as a result, p62$^{dok}$ expression is reduced (totally or partially).

Pharmaceutical compositions which comprise nucleic acids of the present invention and a suitable carrier (e.g., a buffer) are also the subject of this invention. The compositions can include additional components, such as stabilizers.

Proteins and Peptides

The present invention relates to p62$^{dok}$ proteins and polypeptides which can be obtained (isolated) from sources (e.g., cells) in which they occur in nature, produced using recombinant or genetic engineering methods or synthesized chemically. It also relates to pharmaceutical compositions which comprise p62$^{dok}$ protein (constitutively tyrosine phosphorylated or normal tyrosine phosphorylated) and an appropriate carrier, such as a buffer. It may also comprise other components, such as stabilizers and other drugs.

As described herein, Applicants have obtained p62$^{dok}$ from human cells, determined its amino acid sequence and characterized it as to certain of its biochemical features and functions. As described in detail in the examples, p62$^{dok}$ was obtained from a human hematopoietic cell line which expresses an oncogenic tyrosine kinase (specifically, bcr-abl) and a corresponding human hematopoietic cell line which does not express the oncogenic tyrosine kinase (Mo7/p210 and Mo7 cell lines, respectively) by immunoprecipitating GAP from cytoplasmic lysates and analyzing the precipitated complexes by antiphosphotyrosine immunoblotting. Results showed that the corresponding cells in which an oncogenic tyrosine kinase was expressed contained tyrosine phosphorylated p62$^{dok}$ and that cells in which the oncogenic tyrosine kinase was not expressed did not. (Example 1)

p62$^{dok}$ was purified, as described in Example 1, by precipitating GAP from cytoplasmic lysates of $^{32}$P-labeled cells, expressing p210$^{bcr-abl}$, i.e. Mo7/p210 cells, and analyzing the immune complexes by two-dimensional gel electrophoresis. The pattern of spots migrating at 62 kDa on the gel suggested different phosphorylation state isoforms existed. In vitro binding experiments using glutathione-S-transferase fused in frame to the GAP SH2-SH3-SH2 region resulted in the identical two-dimensional pattern of phosphorylated proteins migrating at 62 kDa as that obtained from GAP immunoprecipitations. Purified p62$^{dok}$ was produced using conventional and immuno-affinity chromatography; the final step in purification was separation by two-dimensional gel electrophoresis.

Characterization of p62$^{dok}$ is described in Examples 2 and 3. As can be seen, p62$^{dok}$ is a novel protein with features of a signaling molecule. Tyrosine phosphorylated p62$^{dok}$ (e.g., from cells in which an oncogenic tyrosine kinase is active) associates with GAP; p62$^{dok}$ from cells which lack or do not express an oncogenic tyrosine kinase does not associate with GAP. As is also described in the Examples, p62$^{dok}$ is the 62 kDa GAP-associating protein which is constitutively tyrosine phosphorylated in the hematopoietic progenitor cell population of CML patients. Anti-p62$^{dok}$ antibodies immunoprecipitated a pTyr-containing protein that co-migrated during SDS-PAGE with the tyrosine phosphorylated p62 that co-immunoprecipitated with GAP antibodies from lysates of CML progenitor cells. GAP was present in anti-p62$^{dok}$ immunoprecipitates and p62$^{dok}$ antibodies quantitatively depleted the lysates of a pTyr-containing p62, which provided further evidence that p62$^{dok}$ is the constitutively tyrosine-phosphorylated protein that migrated at 62 kDa in CML progenitor cells. (Example 3)

In one embodiment, the subject protein is normal tyrosine phosphorylated p62$^{dok}$, which is present in normal cells and is not constitutively tyrosine phosphorylated and does not bind GAP in the assay described herein. In an additional embodiment, the protein is aberrantly tyrosine phosphorylated p62$^{dok}$, which is constitutively tyrosine phosphorylated in cells containing active oncogenic tyrosine kinases; it binds GAP. It is possible that tyrosine phosphorylation occurs in normal cells (i.e., it is possible that tyrosine phosphorylation occurs to some extent in normal cells). However, the extent and/or timing of tyrosine phosphorylation of p62$^{dok}$ are characteristically different in cells containing active oncogenic tyrosine kinases from the extent and/or timing in normal cells. Presently, the only biochemical difference identified between p62$^{dok}$ produced in normal cells (p62$^{dok}$ produced in Mo7 cells) and p62$^{dok}$ produced in cells expressing an oncogenic tyrosine kinase (p62$^{dok}$ produced in Mo7/p210 cells) is the presence of phosphotyrosine residues in the latter. Results of a combined immunoprecipitation/immunoblot assay showed that Mo7 p62$^{dok}$ migrates by SDS-PAGE as a singlet of approximately 61 kDa and that two slower migrating forms of p62$^{dok}$ (62 and 64 kDa) were produced in Mo7/p210 cells. Both forms were tyrosine phosphorylated in Mo7/p210 cells and were detected in anti-GAP immunoprecipitates. It appears, however, that only a small proportion of total tyrosine phosphorylated p62$^{dok}$ complexes with GAP. The non-phosphorylated form of p62$^{dok}$ in Mo7 cells was not found associated with GAP.

Proteins or polypeptides referred to herein as "isolated" are proteins or polypeptides purified to a state beyond that in which they exist in cells in which they are produced. "Isolated" proteins or polypeptides include proteins or polypeptides obtained by methods described herein, similar methods or other suitable methods, including essentially pure proteins or polypeptides isolated from the source in which they occur, proteins or polypeptides produced by chemical synthesis (e.g., synthetic peptides), or by combinations of biological and chemical methods, and recombinant proteins or polypeptides which are isolated.

The term "p62$^{dok}$" or "p62$^{dok}$ protein" includes proteins and polypeptides obtained by any of the previously described methods. As used herein, "p62$^{dok}$ protein" refers to naturally occurring or endogenous p62$^{dok}$ protein, proteins having an amino acid sequence which is the same as that of a naturally occurring or endogenous p62$^{dok}$ protein (e.g., recombinant proteins), and functional variants of each of the foregoing (e.g., functional fragments and/or mutants produced via mutagenesis and/or recombinant techniques). Accordingly, as defined herein, the term includes p62$^{dok}$ protein and functional fragments of p62$^{dok}$. Both p62$^{dok}$ protein produced in mammalian (e.g., human) cells which lack an active oncogenic tyrosine kinase (referred to as normal tyrosine phosphorylated p62$^{dok}$) and phosphorylated p62$^{dok}$ produced in mammalian (e.g., human) cells which contain an active oncogenic tyrosine kinase (referred to as constitutively or aberrantly tyrosine phosphorylated p62$^{dok}$) are encompassed in these definitions. Examples of "p62$^{dok}$ protein" of the present invention include proteins having an amino acid sequence as set forth or substantially as set forth in FIG. 1 (SEQ ID NO:2), proteins encoded by p62$^{dok}$-encoding DNA as defined herein and functional portions thereof. The proteins can be obtained in an isolated state of at least about 50% by weight, preferably at least about 75% by weight, and more preferably, in essentially pure form.

Proteins or polypeptides referred to herein as "recombinant" or "recombinantly produced" are proteins or polypeptides produced by the expression of nucleic acids encoding the proteins in a host cell which is modified to contain the nucleic acids encoding the protein (e.g., by transfection with exogenous DNA which encodes p62$^{dok}$ protein) or is modified to express a gene present, but silent or expressed at low levels, in the host cell as obtained (e.g., by transfection with appropriate regulatory sequences which enhance or turn on expression of an endogenous gene). The term also refers to recombinantly produced or recombinant tyrosine phosphorylated p62$^{dok}$, which can be produced in cells which, as obtained or as modified, express p62$^{dok}$ and in which an oncogenic tyrosine kinase is also produced (either in the cells as obtained or as they are modified).

Suitable fragments or mutants of p62$^{dok}$ protein can be identified by screening. For example, the N-terminal, C-terminal, or internal regions of the protein can be deleted in a step-wise fashion and the resulting protein or polypeptide can be screened using a suitable binding assay. A "functional fragment or portion" of p62$^{dok}$ is an isolated protein or polypeptide which has at least one property, activity and/or function characteristic of a p62$^{dok}$ protein, such as migrating at 62 kDa by SDS-PAGE, associating with GAP or binding an anti-GAP antibody.

In one embodiment, p62$^{dok}$ protein or a variant has an amino acid sequence which has at least about 50% identity, more preferably at least about 75% identity, and still more preferably at least about 90% identity, to the amino acid sequence shown in FIG. 1 (SEQ ID NO:2).

In one particular application utilizing proteins and peptides, a drug containing a protein or peptide which mimics p120 ras GAP by binding tyrosine phosphorylated p62$^{dok}$ is introduced into an individual in need of therapy for a condition (e.g., CML) in which a protein (e.g., p62$^{dok}$)is aberrantly tyrosine phosphorylated as the result of the presence of an active oncogenic tyrosine kinase. In this application, the aberrantly tyrosine phosphorylated protein is bound by the "mimic" and is therefore unavailable to bind p120 ras GAP.

Method of Producing Recombinant Proteins

Another aspect of the invention relates to a method of producing p62$^{dok}$ protein or a variant (e.g., portion) thereof. Recombinant p62$^{dok}$ protein can be obtained, for example, by the expression of a recombinant DNA molecule encoding p62$^{dok}$ protein or a variant thereof in a suitable host cell. Alternatively, recombinantly produced p62$^{dok}$ is expressed in a suitable host cell by turning on or enhancing expression of a p62-encoding gene present in (endogenous to) the host cell.

Constructs suitable for the expression of p62$^{dok}$ protein or a variant thereof are also provided. The constructs can be introduced into a suitable host cell. Cells which express a recombinantly-produced p62$^{dok}$ protein or variant thereof, can be produced and maintained in culture. Such cells are useful for a variety of purposes and can be used in the production of p62$^{dok}$ protein for characterization, isolation and/or purification, (e.g., affinity purification), and as immunogens, for instance. Suitable host cells can be procaryotic, including bacterial cells such as *E. coli, B. subtilis* and other suitable bacteria (e.g., Streptococci) or eucaryotic, such as fungal or yeast cells (e.g., *Pichia pastoris, Aspergillus species, Saccharomyces cerevisiae, Schizosaccharomyces pombe, Neurospora crassa*), or other lower eucaryotic cells, and cells of higher eucaryotes, such as those from insects (e.g., Sf9 insect cells) or mammals, including humans (e.g., Chinese hamster ovary cells (CHO), COS cells, HuT 78 cells, 293 cells). See, e.g., Ausubel, F. M. et al., eds. *Current Protocols in Molecular Biology*, Greene Publishing Associates and John Wiley & Sons Inc., (1993).

Host cells which produce p62$^{dok}$ protein or a variant thereof can be produced as follows. A nucleic acid (e.g., DNA) encoding p62$^{dok}$ is inserted into a nucleic acid vector, e.g., a DNA vector, such as a plasmid, virus or other suitable replicon for expression. The resulting vector is introduced into a host cell, using known methods, and the host cell is maintained under conditions appropriate for growth of the host cell and expression of the p62$^{dok}$-encoding DNA. For example, a nucleic acid encoding p62$^{dok}$ protein or a variant thereof can be incorporated into a vector, operably linked to one or more expression control elements, and the construct can be introduced into host cells, which are maintained under conditions suitable for expression of p62$^{dok}$ protein whereby the encoded protein is produced. The construct can be introduced into cells by a method appropriate to the host cell selected (e.g., transformation, transfection, electroporation, infection). The encoded p62$^{dok}$ protein can be isolated from the host cells or medium.

A variety of vectors is available, including vectors which are maintained in single copy or multiple copy, or which become integrated into the host cell chromosome. Suitable expression vectors can contain a number of components, including, but not limited to one or more of the following: an origin of replication; a selectable marker gene; one or more expression control elements, such as a transcriptional control element (e.g., a promoter, an enhancer, terminator), and/or one or more translation signals; a signal sequence or leader sequence for membrane targeting or secretion (of mammalian origin or from a heterologous mammal or non-mammalian species). For example, nucleic acid encoding p62$^{dok}$ protein or a variant thereof could be inserted into any one of the multicloning sites of the pcDNA3 vector (Invitrogen, San Diego). Other acceptable vectors will be readily apparent to one skilled in the art.

Antibodies

The present invention also relates to antibodies, both polyclonal and monoclonal, which bind p62$^{dok}$ in vitro and/or in vivo and, optionally, inhibit an activity or function characteristic of p62$^{dok}$. In one embodiment, the antibodies bind constitutively tyrosine phosphorylated p62$^{dok}$ or normal tyrosine phosphorylated p62$^{dok}$ but not both, thus making them useful, for example, in assays in which the two forms of p62$^{dok}$ are to be distinguished (e.g., in an immunoassay carried out to determine if cells are progressing toward a transformed state). The present invention further relates to pharmaceutical compositions which comprise p62$^{dok}$ antibodies and a suitable carrier, such as a buffer; they can also include further components, such as stabilizers.

Preferably, the antibodies can bind mammalian (e.g. human) p62$^{dok}$ with high affinity (for example, a Ka in the range of about 1–10 nM, or a Kd in the range of about $1\times10^{-8}$ to $1\times10^{-10}$ mol$^{-1}$).

The antibodies of the present invention are useful in a variety of applications, including separation techniques, research and diagnostic and therapeutic applications. For instance, they can be used to isolate and/or purify p62$^{dok}$ or variants thereof (e.g., by affinity purification or other suitable methods), and to study p62$^{dok}$ structure (e.g., conformation) and function.

In addition, antibodies of the present invention can be used to detect and/or measure the level of p62$^{dok}$ in a sample (e.g., tissue or body fluid) obtained from an individual (e.g., a human). For example, a sample (e.g., tissue and/or fluid) can be obtained from an individual and a suitable immunological method can be used to detect and/or measure p62$^{dok}$ levels of constitutively tyrosine phosphorylated p62$^{dok}$ or normal tyrosine phosphorylated p62$^{dok}$ In one embodiment, a method of detecting one or both forms of p62$^{dok}$ in a sample is carried out by obtaining a sample of tissue or cells from an individual; treating the sample to render p62$^{dok}$ available for binding by antibodies; contacting the treated sample with a p62$^{dok}$ antibody (e.g., an antibody which binds aberrantly tyrosine phosphorylated p62$^{dok}$, normal tyrosine phosphorylated p62$^{dok}$ or both forms) under conditions suitable for binding of the antibody to p62$^{dok}$ and formation of p62$^{dok}$/antibody complexes; and detecting p62$^{dok}$/antibody complexes which are formed. The presence of complexes indicates that p62$^{dok}$ is present in the sample; the antibody used will determine which form(s) of p62$^{dok}$ is/are present in the complexes.

In an application of the method, antibodies which bind p62$^{dok}$ are used to analyze tissues or cells in mammals for p62$^{dok}$ reactivity and/or expression (e.g., immunohistologically). Thus, the antibodies of the present invention are useful in immunological diagnostic methods of assessing expression of p62$^{dok}$ (especially tyrosine-phosphorylated p62$^{dok}$) in normal tissues or cells and cancerous tissues or cells.

p62$^{dok}$ antibodies also have therapeutic uses. A p62$^{dok}$ antibody can be administered in an amount effective to inhibit p62$^{dok}$ activity. For therapy, an effective amount is sufficient to achieve the desired therapeutic and/or prophylactic effect (such as an amount sufficient to reduce or prevent tyrosine phosphorylated p62$^{dok}$ function or activity, such as binding to GAP). The antibody can be administered in a single dose or multiple doses. The dosage can be determined by methods known in the art and is dependent, for example, upon the individual's age, sensitivity, tolerance and overall well-being. Suitable dosages for antibodies can be from 0.1–1.0 mg/kg body weight per treatment.

According to the method, an antibody can be administered to an individual (e.g., a human) alone or in conjunction with another agent, which is administered before, along with or subsequent to administration of the antibody.

Administration of Compositions of the Present Invention

Compositions of the present invention can be administered by a variety of routes, including, but not limited to, parenteral (e.g., injection, including but not limited to, intravenous, intraarterial, intramuscular, subcutaneous; inhalation, including but not limited to, intrabronchial, intranasal or oral inhalation, intranasal drops; topical) and non-parenteral (e.g., oral, including but not limited to, dietary; rectal).

The formulation used will vary according to the route of administration selected (e.g., solution, emulsion, capsule). An appropriate composition comprising the nucleic acids, proteins or antibodies to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers. See, generally, *Remington's Pharmaceutical Science,* 16th Edition, Mack, Ed. (1980). For inhalation, the compound can be solubilized and loaded into a suitable dispenser for administration (e.g., an atomizer, nebulizer or pressurized aerosol dispenser). Nucleic acids, proteins and antibodies can be administered individually, together or in combination with other drugs or agents (e.g., other chemotherapeutic agents, immune system enhancers).

The present invention is further illustrated by the following examples, which are not intended to be limiting in any way.

Methods and Materials

The methods and materials described below were used in carrying out the work described in the examples which follow.

Immunoprecipitation and Western Blot Analysis

The Mo7 cell line, and a derivative of Mo7 which expresses p210$^{bcr-abl}$, Mo7/p210 (provided by Dr. Brian Druker, Portland, Ore.), were maintained in RPMI (Gibco) +10% Fetal Clone III (Hyclone) at 37° C. and 5% CO$_2$. Avanzi, G. C. et al., *Brit. J. Hemat.,* 69:359–366 (1988); Matsuguchi, T. et al., *J. Biol. Chem.,* 269:5016–5021 (1994). The Mo7 growth media contained 10 ng/ml recombinant GM-CSF (provided by Genetics Institute, Boston, Mass.).

For immunoprecipitations, cells were washed twice in PBS containing 1 mM Na$_3$VO$_4$ and 100 μM phenylarsine oxide (PAO), and lysed. Lysis buffer (LB) was 50 mM Tris-HCl, pH 7.6, 150 mM NaCl, 5 mM EDTA, 1 mM EGTA, 1% Triton X-100, 0.5 μg/ml leupeptin, 50 μg/ml soybean trypsin inhibitor, 0.1 μg/ml aprotinin, 100 μg/ml phenymethyl sulfonyl fluoride, 1 mM Na$_3$VO$_4$, and 100 AM PAO. Prior to immunoprecipitations, cell lysates were clarified by centrifugation at 14,000 rpm at 4° C. All experiments were carried out with equal protein concentration (750 μg protein/0.5 ml LB). Lysates were precleared by 15 min rotation at 4° C. with Protein A-Sepharose (Pierce). Following addition of antibody, immune complexes were allowed to form during a 90 minute rotation at 4° C. After Protein A-Sepharose was added, rotation at 4° C. was continued for 1 hr; then, the beads were washed five times in buffer containing 20 mM Tris-HCl, pH 7.6, 150 mM NaCl, 1 mM EDTA, 0.1% Triton X-100, 100 μg/ml PMSF, and 1 mM Na$_3$VO$_4$. SDS-PAGE and western transfer were done according to standard protocols. Harlow, E. and Lane, D., *Antibodies: A Laboratory Manual,* Cold Spring Harbor Laboratory Press (1988). Following transfer, the nitrocellulose was blocked for 1 hour in TBST containing 3k BSA (Sigma), incubated for 1 hour with blocking buffer containing primary antibody, washed with TBST, incubated for 1 hour with secondary antibody, again washed with TBST, and developed by the ECL method (Amersham). The following antibodies were used for the precipitations: anti-GAP mAb B4F8 (Santa Cruz); anti-phosphotyrosine mAb PY20 (ICN); anti-p62 polyclonal antibody SC-108 (Santa Cruz); and anti-p62$^{dok}$ polyclonal antibody (see below). The following antibodies were used for immunoblotting: anti-phosphotyrosine polyclonal antibody B5 (Kozma, L. M. et al., *Methods in Enz.,* 201:28–43 (1991)), anti-PTyr mAb 4G10 (UBI), anti-GAP polyclonal antibody RH6-2A, and anti-p62$^{dok}$ polyclonal antibody.

To radiolabel proteins, cells were washed twice with PBS, and resuspended in phosphate-free media containing 10% dialyzed fetal calf serum (Gibco) and 1 mCi/ml $^{32}$P-orthophosphate (ICN). Following a two hour labeling period, cells were washed twice as above, and resuspended in LB at 10$^7$ cells/IP. Immunoprecipitations were conducted as described above. For phosphoamino acid analysis, labeled GAT 62 was transferred to PVDF and processed exactly as described. van der Geer, P. et al., *Protein Phosphorylation, A Practical Approach,* D. Grahame Hardie, ed., IRL Press, pp. 31–59 (1993). Two dimensional electrophoresis was conducted exactly as described. O'Farrell, Patrick H., *J. Biol. Chem.,* 250:4007–4021 (1975); Garrels, J., "Quantitative two-diemensional gel electrophoresis of proteins." In *Methods in Enzymology* 100: *Recombinant DNA(b),* R. Wu et al., eds., Academic Press, San Diego (1983), pp. 411–423.

Peptide competition experiments were conducted by incubating 1 mg of either antigenic peptide or unrelated peptide (CLIGEGTYGVVYK), SEQ ID NO.:14, with cell lysate prior to immunoprecipitation, or with nitrocellulose prior to western blotting.

Hematopoietic progenitor cells from CML patients in the chronic phase were isolated and processed for immunoprecipitation exactly as described. Wisniewski, D. et al., *Leukemia,* 10:229–237 (1996).

Purification of p62$^{dok}$

Fifty liters of Mo7/p210 cells were grown to a density of 2×10$^6$/ml in RPMI containing 20 mM Hepes (Gibco) and 5t Fetal Clone III (Hyclone), harvested by centrifugation and treated for 10 min at 37° with 100 μM PAO in growth media. The cells were then washed as above and lysed in LB containing 50 mM NaCl. The lysate was adjusted to 3M urea by the addition of buffer containing 6M urea, 50 mM Tris-HCl, pH 8.3, 5 mM EDTA, 1 mM EGTA, following which it was loaded onto a Q Sepharose HP (Pharmacia) column (19×5 cm). Bound proteins were eluted from the column with an increasing linear gradient of NaCl, from 25 mM NaCl to 600 mM NaCl. Alternatively, cytoplasmic proteins were batch absorbed to Q Sepharose HP and step-eluted with buffer containing 350 mM NaCl. Fractions containing p62$^{dok}$ were pooled, adjusted to 50 mM acetate, pH 4.6, by the addition of 2 volumes of 75 mM acetic acid, 5 mM EDTA, 3M urea, and loaded onto an SP column (5×2.5 cm, TosoHaas). Bound proteins were eluted with an increasing linear gradient of NaCl, from 100 mM NaCl to 800 mM NaCl. Alternatively, pooled fractions were batch absorbed to SP ToyoPearl and step-eluted with buffer containing 300 mM NaCl. Fractions containing p62$^{dok}$ were pooled and total protein was precipitated with ice-cold acetone. The precipitate was resuspended in 8M urea, dialyzed against 50 mM Tris-HCl, pH 7.6, 150 mM NaCl, 5 mM EDTA, 0.1% Triton X-100, 0.5 mM Na$_3$VO$_4$ and loaded onto an anti-pTyr antibody column, 4G10-Sepharose (UBI). The column was washed with load buffer and distilled water, and bound proteins were eluted by the addition of 4% acetic acid. Following removal of the solvent by lyophilization, the eluted material was resolved by two-dimensional gel electrophoresis. The gel was stained with 0.05% Coomassie Brilliant Blue G (Sigma) in 5% AcOH-10% MeOH, and destained with the same solution lacking Coomassie dye.

Peptide Sequencing

The acrylamide gel containing the spots of Coomassie-stained p62$^{dok}$ was excised from several gels, and washed sequentially with distilled water and 50% MeOH. The protein in the gel was digested with 500 ng Achromobacter protease I (Wako) in 0.05M Tris-HCl, pH 9.0, 0.1% Tween-20 for 20 hours at 30° C., then the resulting peptide fragments were extracted from the gel with a solution containing 50% acetonitrile and 0.064% TFA, and separated by HPLC using a Vydac C18 column (1.0×250 mm, 10 pm, 300 Å). Peptides were eluted with an increasing gradient of acetonitrile. HPLC fractions containing various peaks of eluted peptides were individually applied to an automated protein sequencer (ABI model 494).

cDNA Cloning

Total RNA, extracted from Mo7/p210 cells with RNAzol (Tel-Test, Inc.), was used to make random primed cDNA for the RT-PCR. Reverse transcription was carried out at 50° C. with Superscript II (Gibco BRL) according to the instructions of the manufacturer. Three rounds of nested PCR were conducted with the primers listed below from 5' to 3' of the cDNA, with (S) indicating sequence of the sense strand, (C) indicating sequence of the complementary strand and I indicating inosine. Round 1: K29N1, TGGGCIGTIT/CTITAT/CCC(S) [SEQ ID NO.:10] and K31C1, TTIAG/AIAG/AIAG/AT/CT/CTGT/CTGT/CTGA/G/C/TGC(C) [SEQ ID NO.:12]; round 2: K29N2, GTIT/CTITAT/CCCT/AGCIT/AC/GCCICATGG(S) [SEQ ID NO.:11] and K31C2, T/CTGT/CTGT/CTGIGCATGT/CTCA/GTA (C) [SEQ ID NO.:13]; round 3: K29N3, CATGGIGTIGCIA/CGIT/CTIGAA/GTT(S) [SEQ ID NO.:14] and K31C3, T/CTGIGCATGT/CTCA/GTAIAG/AA/GTC(C) [SEQ ID NO.:15].

The resulting PCR was radiolabeled and used as a probe to screen an oligo(dT)-primed human teratocarcinoma cDNA library. Skowronski, J. et al., *Mol. and Cell Biology*, 8: 1385–1397 (1988). Hybridization was performed in buffer containing 6× SSC, 0.1% SDS, 5× Denhardt's solution, and 20 µg/ml sonicated salmon sperm DNA (Sigma) at 67° C. The following washes were performed at the same temperature: 30 min, 2× SSC, 0.1 SDS; 30 min, 1× SSC, 0.1 SDS; 30 min, 0.2× SSC, 0.1% SDS. Positive clones were isolated, phage DNA was purified, cDNA inserts were excised by restriction enzyme digest, and the longest insert was cloned into a plasmid vector (pBluescript, SK-) for DNA sequencing, all using standard methodologies. Sambrook, J. et al., *Molecular Cloning: A Laboratory Manual*, Cold Spring Harbor Laboratory Press (1989). For Northern analysis, blots of poly A+ RNA from different human tissues (Clontech) were probed with a radiolabeled 1526 bp fragment of Dok cDNA obtained by PCR, according to the instructions of the manufacturer. The cDNA sequence has been submitted to Genbank (Accession number U70987).

Anti-p62$^{dok}$ Antibodies

A peptide with a C-terminal cysteine was synthesized (PQGPAFPEPGTATGSC [SEQ ID NO.:16]; BioSynthesis, Inc.), conjugated to maleimide activated KLH (Pierce), and used to immunize rabbits (Hazelton). To affinity purify anti-peptide antibodies, ammonium sulfate to 50% saturation was added to sera. Precipitated material was taken up in PBS, dialyzed against a large volume of PBS, and passed over a resin to which peptide had been coupled (Sulfo-link Coupling Gel, Pierce). Antibodies were released from the column by addition of 0.1 M glycine, pH 2.5.

Stimulation with c-Kit Ligand

Exponentially growing Mo7 cells (10$^7$/IP) were washed free of growth factor and incubated for 16 hours at 370 in IMDM (Gibco) containing 1% fetal calf serum (Gibco). Cells were then pelleted by centrifugation, resuspended in IMDM +1% serum and exposed to c-kit ligand (100 ng/ml) for 5 minutes at 37°. Cells were then washed once with PBS and processed for immunoprecipitation/western blot analysis exactly as described. Wisniewski, D., et al., *Leukemia*, 10: 229–237 (1996). Human recombinant c-kit ligand was from Immunex Corp., Seattle.

EXAMPLE 1

Identification and Purification of p62$^{dok}$

Following the initial observation of tyrosine phosphorylated p62 in primary CML progenitor cells (Wisniewski, D., et al., *Leukemia*, 8:688–693 (1994)), the Mo7 cell line and a derivative of Mo7 expressing p210$^{bcr-abl}$, Mo7/p210 (Avanzi, G. C., et al., *British Journal of Haematology*, 69:359–366 (1988); Matsuguchi, T., et al., *J. Biol. Chem.* 269:5016–5021 (1994)), was utilized to determine whether or not the p62 protein was similar to the molecule heretofore known as the GAP-associated p62. GAP was immunoprecipitated from cytoplasmic lysates of Mo7 cells and cells expressing p210$^{bcr-abl}$, i.e. Mo7/p210 cells. The precipitated complexes were then analyzed by anti-phosphotyrosine immunoblotting. Ellis, C., et al., *Nature* 343:377–381 (1990). Anti-GAP immunoprecipitates from Mo7/p210 lysates, but not from Mo7 lysates, contained tyrosine phosphorylated p62 which migrated as a doublet. The GAP-associated doublet was also observed in anti-phosphotyrosine immunoprecipitates from lysates of Mo7/p210 cells, but not from Mo7 cells. However, a similar protein in complexes precipitated by rabbit polyclonal antibodies against the molecule previously reported as the GAP-associated p62 (Wong, G., et al., *Cell* 69: 551–558 (1992)) were not detectable. The same polyclonal antibodies were unable to immunoblot a specific polypeptide in anti-GAP immunoprecipitates, nor could they precipitate a phosphorylated 62 kDa polypeptide from lysates of $^{32}$P-labeled Mo7/p210 cells. As a result of these immunological discrepancies the p62 protein, henceforth called p62 protein downstream of tyrosine kinases (p62$^{dok}$), was purified.

To purify p62$^{dok}$, an assay for the identity of the protein was developed. GAP was precipitated from cytoplasmic lysates of $^{32}$P-labeled cells expressing p210$^{bcr-abl}$ and the immune complexes were analyzed by two-dimensional gel electrophoresis. A characteristic pattern of spots migrating at 62 kDa resulted, suggestive of different phosphorylation state isoforms. Because p62 previously had been shown to bind to the SH2-SH3-SH2 region of GAP (Marengere, L. E. M. and Pawson, T., *J. Biol. Chem.*, 267:22779–22786 (1992)), in vitro binding experiments were conducted, utilizing GST fused in frame to the GAP SH2-SH3-SH2 region. These experiments yielded the identical two-dimensional pattern of phosphorylated proteins migrating at 62 kDa as that obtained from GAP immunoprecipitations. A combination of conventional and immuno-affinity chromatography was used to purify p62$^{dok}$ Lysates of Mo7/p210 cells were passed sequentially over two ion-exchange columns, following which an anti-pTyr antibody column was used to capture remaining tyrosine phosphorylated proteins. As a final step in the purification, proteins eluted from the antibody column were separated by two-dimensional gel electrophoresis.

EXAMPLE 2

Assessment of P62$^{dok}$ as a Potential Signaling Molecule

Coomassie-stained p62$^{dok}$ was excised from a gel and digested with protease to yield peptide fragments, five of which were sequenced. Degenerate oligonucleotide primers were designed based on the amino acid sequence of two peptides, and used in RT-PCR to amplify a fragment of p62$^{dok}$ cDNA. After three rounds of nested PCR, a 900 bp product was obtained, which was used to screen a human teratocarcinoma cDNA library. Skowronski, J. et al., *Mol. Cell Biology*, 8:1385–1397 (1988). A screen of 750,000 individual phage clones yielded five positives. The amino acid sequence encoded by the longest insert representing Dok cDNA is illustrated in FIG. 2. The cDNA encoded a novel protein of 481 amino acids with a predicted molecular mass of 53 kDa. In vitro translated p62$^{dok}$ migrated at ~61 kDa by SDS-PAGE, similar to p62$^{dok}$ immunoprecipitated from Mo7 cells by anti-p62$^{dok}$ antibodies. A profile search utilizing the Prosite profile database detected a putative pleckstrin homology (PH) domain (Mussachio, A. et al., *TIBS*, 18:343–348 (1993)) at the extreme N terminus of p62$^{dok}$ Aside from this, no significant homology between p62$^{dok}$ and other known proteins was found. p62$^{dok}$ has 15 tyrosines, 10 of which are located within a C-terminal stretch one third the length of the molecule. Kyte-Doolittle hydrophobicity analysis indicates that this region of p62$^{dok}$ is more hydrophilic than other portions of the molecule. Additionally, p62$^{dok}$ is relatively proline-rich, with ten PXXP motifs. The PXXP motif has been demonstrated to be the most conserved motif within known SH3 domain ligands (Yu, H. et al., *Cell*, 76:933–945 (1994)), suggesting that p62$^{dok}$ might form signaling complexes with other molecules that contain SH3 domains.

Recently, the substrate specificities of a variety of tyrosine kinases were proposed. Songyang, Z. et al., *Nature*, 373:536–539 (1995). The optimal peptide substrate of the c-abl kinase was found to be I/V/LYAAP/F, SEQ ID NO.:17. Although none of the tyrosines of p62$^{dok}$ have adjacent residues exactly matching this consensus sequence, residues 295–299 (LYAEP) [SEQ ID NO.:18] are a close match. Additionally, three tyrosines are within the context I/LYXXP, SEQ ID NO.:19. Therefore, p62$^{dok}$ might be a direct substrate of p210$^{bcr-abl}$ In addition, the recognition specificities of the SH2 domains of a variety of known signaling molecules have been proposed. Songyang, Z. et al., *Cell*, 72:767–778 (1993); Songyang, Z. et al., *Mol. Cell Biol.*, 14:2777–2785 (1994). One of the p62$^{dok}$ tyrosines (residue 449) is in a context which is consistent with the proposed SH2 recognition motifs. This most C-terminal tyrosine is located within the sequence SALYSQVQ, SEQ ID NO.:20, suggesting that this site, if phosphorylated, might associate with the SH2 domain of csk, the c-terminal src kinase. Evidence for the direct interaction between the SH2 domain of csk and the GAP-associated p62 has been presented. Neet, K. and Hunter, T., *Mol. Cell Biol.*, 15:4908–4920 (1995). It is possible that, in addition to GAP, tyrosine phosphorylated p62$^{dok}$ forms a complex with csk and other yet unknown SH2 domain-containing signaling proteins.

To demonstrate that the clone isolated encoded a GAP-associated p62, rabbit polyclonal antibodies were raised against a synthetic peptide derived from the sequence of p62$^{dok}$ The antigenic peptide specifically blocked the ability of the antibody to precipitate this doublet, while an unrelated peptide had no effect. Furthermore, anti-p62$^{dok}$ antibodies detected a 62 kDa doublet in immunoblots of proteins that co-immunoprecipitated with antibodies directed against GAP, and the antigenic peptide specifically blocked the ability of the antibody to detect this doublet, while an unrelated peptide had no effect. Taken together, these data demonstrated that the antibodies recognized a constitutively-tyrosine phosphorylated, GAP-associated p62 from Mo7/p210 cells.

Given the important signaling role that tyrosine kinases play in hematopoietic growth control, it is not surprising that the sudden appearance of a novel tyrosine kinase activity (e.g. p210$^{bcr-abl}$) within a single primitive progenitor cell would perturb the intracellular signaling cascades that ensure orderly hematopoiesis. Bolen, J. B. et al., *FASEB J.*, 6:3403–3409 (1992). The two fused portions of p210$^{bcr-abl}$ are each derived from molecules which themselves contain some of the modular features common to signaling proteins. Cohen, G. B. et al., *Cell*, 80:237–248 (1995). In addition, bcr-abl is a large molecule that is extensively tyrosine phosphorylated, providing numerous potential docking sites for SH2 domain-containing proteins. Thus, this activity could interact with various components of pre-existing signaling networks within a primitive stem cell. Pawson, T., *Nature*, 373:573–580 (1995).

As a potential signaling molecule, p62$^{dok}$ has several noteworthy features. It contains a putative pleckstrin homology (PH) domain at its extreme amino terminus, comprising residues 3–119. Mussachio, A. et al., *TIBS*, 18:343–348 (1993). A variety of proteins involved in signaling and/or cytoskeletal organization contain PH domains, among them GAP. A proposed function of the PH domain is to mediate protein-protein interactions. Pawson, T., *Nature*, 373:573–580 (1995). Additionally, it is thought that these conserved structural domains mediate interactions with cellular membranes, possibly by binding to different inositol phosphate components of the lipid bilayer. Lemmon, M. A. et al., *Cell*, 85:621–624 (1996). For example, the PH domain of PLC$\delta_1$ binds specifically and with high affinity to PtdIns$_2$. Lemmon, M. A. et al., *PNAS*, 92:10472–10476 (1995). Thus, the function of the N-terminal region of p62$^{dok}$ might be to serve as a modular binding domain, either localizing the molecule to the cell surface or directing its interaction with a variety of proteins. If the function of the PH domain of p62$^{dok}$ is to bind other proteins or components of the membrane, then the C-terminal portion of the molecule would likely be positioned to interact with a variety of proteins and/or small molecules within the cytosol. Therefore, it might contain a critical functional domain of the polypeptide. The majority of tyrosines within p62$^{dok}$ are located in the C-terminal half of the molecule, and it is speculated that they are available as targets for the activity of neighboring tyrosine kinases, for example p210$^{bcr-abl}$ itself. It is possible that these tyrosines, when phosphorylated, serve as docking sites for proteins which contain SH2 domains. In addition to the C-terminal tyrosines, p62$^{dok}$ contains ten PXXP motifs. Because PXXP is the core conserved sequence of proline-rich regions which are recognized by SH3 domains, it is possible that p62$^{dok}$ can interact with signaling molecules containing SH3 domains. Yu, H. et al., *Cell,* 76:933–945 (1994).

p62$^{dok}$ binds in vitro to the N-terminus of GAP, suggesting that tyrosine phosphorylated p62$^{dok}$ interacts in vivo with the SH2 domains of GAP. Originally, GAP was identified based on its ability to increase the intrinsic GTPase activity of ras. Trahey, M. and McCormick, F., *Science,* 238:542–545 (1987). Its catalytic domain is located in the C-terminal half of the molecule. In recent years, evidence has accumulated that the N-terminus of GAP plays a functional role in intracellular signaling, separate and distinct from the C-terminus. Valius, M. et al., *Mol. Cell Biol.,* 15:3058–3071 (1995). For example, overexpression of the N-terminal region of GAP in Rat-2 cells resulted in disruption of the actin cytoskeleton and focal contacts, as well as decreased fibronectin binding and cell adhesion. McGlade, J. et al., *EMBO J.,* 12:3073–3081 (1993). Therefore, it is possible that constitutive p62$^{dok}$ association with GAP might deregulate a signaling network involving the N-terminus of GAP. Currently, it is unclear whether the association of p62$^{dok}$ with GAP is due solely to a direct interaction between a phosphotyrosine of the former and the SH2 region(s) of the latter. In view of the PXXP motifs of p62$^{dok}$, it is possible that the SH3 domain of GAP stabilizes the association of the two molecules.

EXAMPLE 3

Analysis of p62$^{dok}$

At present, the only biochemical difference between Mo7 p62$^{dok}$ and Mo7/p210 p62$^{dok}$ detected is the presence of phosphotyrosine residues in the latter population. Both populations contained phosphoserine, although whether identical serine residues are phosphorylated is unknown. Moreover, a combined immunoprecipitation/immunoblot assay indicated that Mo7 p62$^{dok}$ migrated by SDS-PAGE as a singlet of ~61 kDa, whereas it shifted completely to two slower migrating forms of 62 and 64 kDa in Mo7/p210 cells. This quantitative shift suggests that the entire population of p62$^{dok}$ within the cell is altered by the presence of p210$^{bcr-abl}$. Both forms of p62$^{dok}$ in p210$^{bcr-abl}$ containing cells were tyrosine-phosphorylated, and both forms could be detected in anti-GAP immunoprecipitates and in anti-pTyr immunoprecipitates. However, preliminary data indicates that only a small proportion of total tyrosine phosphorylated p62$^{dok}$ complexes with GAP. The faster migrating, non-tyrosine phosphorylated form of p62$^{dok}$ in Mo7 cells was not found associated with GAP.

The next step was to determine whether or not p62$^{dok}$ was involved in a signal transduction pathway initiated by a receptor tyrosine kinase. Previous studies had implicated a 62 kDa protein as a downstream target of c-kit receptor kinase activity in human primary lineage negative normal hematopoietic progenitor cells. Wisniewski, D. et al., *Leukemia,* 10:229–237 (1996). The c-kit receptor is a type II receptor tyrosine kinase that is structurally related to the PDGF receptor. van der Geer, P. et al., *In Protein Phosphorylation, a Practical Approach*, D. Grahame Hardie, ed. (Oxford, England: IRL Press), pp. 31–59 (1993). Its ligand, c-kit ligand (steel factor, MGF, stem cell factor), has pleiotropic effects on the development of diverse cell types. Galli, S. J. et al., *Adv. Immunol.,* 55:1–96 (1994). Among other influences, it promotes hematopoietic progenitor cell survival, and acts synergistically with GM-CSF, G-CSF, IL-3, and Epo to enhance in vitro colony formation by early progenitors of various lineages. McNiece, I. K. et al., *Exp. Hematol,* 19:226–231 (1991). p62$^{dok}$ was found to be rapidly tyrosine phosphorylated after stimulation of Mo7 cells with c-kit ligand. This result indicates that tyrosine phosphorylation of p62$^{dok}$ is a rapid biochemical event, occurring shortly after a receptor tyrosine kinase is activated.

The next step was to determine whether or not p62$^{dok}$ was the tyrosine-phosphorylated p62 previously identified in lysates of primary chronic phase CML progenitor cells. Wisniewski, D. et al., *Leukemia,* 8:688–693 (1994). Anti-p62$^{dok}$ antibodies immunoprecipitated a pTyr-containing protein that co-migrated during SDS-PAGE with the tyrosine phosphorylated p62 that co-immunoprecipitated with GAP antibodies from lysates of CML progenitor cells. In addition, GAP could be observed in anti-p62$^{dok}$ immunoprecipitates. Furthermore, p62$^{dok}$ antibodies quantitatively depleted the lysates of a pTyr-containing p62 to make it likely that p62$^{dok}$ was the constitutively tyrosine-phosphorylated protein migrating at 62 kDa in CML progenitor cells. Based on this experimental data, p62$^{dok}$ is concluded to be the 62 kDa GAP-associating protein previously reported to be constitutively tyrosine phosphorylated in the hematopoietic progenitor cell population of CML patients.

Current evidence suggests that p62$^{dok}$ is a substrate of the constitutive tyrosine kinase activity of p210$^{bcr-abl}$, and that its abnormal modification within Ph$^+$ primitive hematopoietic progenitors plays a role in the complex physiological disorder manifested in the chronic phase of CML. Constitutive tyrosine phosphorylation of p62 is detected in all primary chronic phase CML primitive blasts observed to date. Wisniewski, D. et al., *Leukemia,* 10:229–237 (1996).

Although at present the biological function of p62$^{dok}$ is unknown, several lines of evidence suggest that it plays a role in distinct signal transduction networks, most likely as a component of a signaling cascade initiated by receptor or membrane-associated tyrosine kinases. It is possible that p62$^{dok}$ is the human homologue of the protein widely known as the classical GAP-associated p62 (Lock, P. et al., *Cell,* 84:23–24 (1996)), and that many of its properties are similar to those heretofore attributed to the latter molecule. The rapid tyrosine phosphorylation of the GAP-associated p62 in Rat-l fibroblasts upon EGF stimulation and in Rat-2 fibroblasts upon PDGF stimulation has been reported. Ellis, C. et al., *Nature,* 343:377–381 (1990). Using a different system, Filvaroff et al., demonstrated the tyrosine phosphorylation of a GAP-associated p62 in primary mouse keratinocytes as one of the initial events in calcium-induced terminal differentiation. Filvaroff et al. (1992). Other agents, such as EGF, TGFβ, and phorbol ester, did not induce phosphorylation of p62, although they did result in the tyrosine phosphorylation of the signaling molecules PLCγ and PI3 kinase. These latter enzymes were unaffected by calcium stimulation. Finally, it has been demonstrated that c-kit ligand induces the rapid tyrosine phosphorylation of a p62, most likely the GAP-associated p62, in primitive hematopoietic progenitors.

Wisniewski, D. et al., Leukemia, 10:229–237 (1996). Herein, it is shown that p62$^{dok}$ is rapidly tyrosine phosphorylated upon activation of the c-kit receptor tyrosine kinase, suggesting that it lies on a signaling pathway downstream of the c-kit receptor. In light of the constitutive tyrosine phosphorylation of p62$^{dok}$ in hematopoietic progenitors containing p210$^{bcr-abl}$, it is provocative that some of the biological effects of both p210$^{bcr-abl}$ and c-kit ligand appear to be similar, and these effects are manifested in a relatively mature stem cell population at the time of lineage commitment rather than at the level of self-renewing stem cell. Strife, A. et al., Cancer Res., 53:401–409 (1993). Furthermore, because tyrosine phosphorylation of p62$^{dok}$ was observed in chronic phase progenitor cells from all CML patients tested (Wisniewski, D. et al., Leukemia, 10:229–237 (1996)), it is possible that aberrant or untimely tyrosine phosphorylation of p62$^{dok}$ is a key step in the development of the chronic phase of CML.

Numerous investigators working with a variety of transformed cell lines have observed the tyrosine phosphorylation of a p62 and its association with GAP. Ellis, C. et al., Nature, 343:377–381 (1990); Moran, M. F. et al., Mol. Cell Biol., 11:1804–1812 (1991). Murine p62$^{dok}$ has been identified and demonstrated to be directly associated with the v-abl activated tyrosine kinase. Yamanashi, Y. and Baltimore, D., Cell, Jan. 24, 1997. In addition, the extent to which p62 is tyrosine phosphorylated has been shown to correlate with the transforming capabilities of a number of different oncogenes, including v-src, v-abl, v-fps, and v-mos. Ellis, C. et al., Nature, 343:377–381 (1990); Lugo et al. (1990); Zhao, J. F. et al., Oncogene, 11:161–173 (1995). The widespread correlation between constitutive tyrosine phosphorylation of p62$^{dok}$ and the transformed phenotype suggests that p62$^{dok}$ plays an important role in mitogenic signaling, and that the aberrant phosphorylation of p62$^{dok}$ might contribute to the progression of different human diseases.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. Isolated DNA which encodes $p62^{dok}$ protein, wherein the isolated DNA is selected from the group consisting of: a) DNA having the nucleotide sequence of SEQ ID NO.: 1; b) DNA which, due to the degeneracy of the genetic code, encodes the amino acid sequence encoded by DNA having the nucleotide sequence of SEQ ID NO.: 1; and c) DNA which encodes the amino acid sequence of SEQ ID NO.: 2.

2. The isolated DNA of claim 1 which is cDNA.

3. The isolated DNA which is the complement of DNA of claim 1.

4. An-isolated nucleic acid molecule which hybridizes under very stringent conditions to DNA selected from the group consisting of:

a) DNA having the nucleotide sequence of SEQ ID NO.: 1;
   b) DNA which, due to the degeneracy of the genetic code, encodes the amino acid sequence encoded by DNA comprising SEQ ID NO.: 1;
   c) DNA which encodes the amino acid sequence of SEQ ID NO.: 2;
   d) the complement of SEQ ID NO.: 1;
   e) the complement of b); and
   f) the complement of DNA which encodes the amino acid sequence of SEQ ID NO.: 2;

wherein said very stringent conditions comprise forming a hybridization complex at 67° C. in a buffer comprising 6× SSC, 0.1% SDS, 5× Denhardt's solution and 20 μl salmon sperm DNA and washing the resulting complex in a series of 3 wash buffers comprising 2× SSC, 0.1% SDS; 1× SSC, 0.1% SDS and 0.2% SSC, 0.1% SDS for 30 minutes or wash at 67° C.

5. An expression vector comprising isolated DNA of claim 1, which expresses the DNA in a mammalian host cell.

6. An expression vector comprising a isolated nucleic acid molecule of claim 4.

7. A mammalian host cell transfected with an expression vector of claim 6, wherein the nucleic acid molecule is expressed in the mammalian host cell.

* * * * *

UNITED STATES PATENT AND TRADEMARK OFFICE
CERTIFICATE OF CORRECTION

PATENT NO. : 6,100,386
DATED : August 8, 2000
INVENTOR(S) : Nicholas A. Carpino, et al.

It is certified that error appears in the above-identified patent and that said Letters Patent is hereby corrected as shown below:

Column 38, Claim 4, line 45, delete "or" and insert --per--
Column 38, Claim 6, line 49, delete "a" and insert --an--

Signed and Sealed this

Seventeenth Day of April, 2001

Attest:

NICHOLAS P. GODICI

Attesting Officer  Acting Director of the United States Patent and Trademark Office

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 1446 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1..1443

(xi) SEQUENCE DESCRIPTION: SEQ ID NO:1:

```
ATG GAC GGA GCA GTG ATG GAA GGG CCG CTT TTT TTG CAG AGT CAG CGC        48
Met Asp Gly Ala Val Met Glu Gly Pro Leu Phe Leu Gln Ser Gln Arg
 1               5                  10                  15

TTT GGG ACC AAG AGG TGG AGG AAG ACC TGG GCC GTG CTC TAC CCG GCC        96
Phe Gly Thr Lys Arg Trp Arg Lys Thr Trp Ala Val Leu Tyr Pro Ala
                20                  25                  30

AGT CCC CAC GGC GTA GCG CGG CTC GAG TTC TTT GAC CAT AAG GGG TCG       144
Ser Pro His Gly Val Ala Arg Leu Glu Phe Phe Asp His Lys Gly Ser
            35                  40                  45

AGC TCT GGG GGT GGC CGA GGG AGC TCG CGC CGC CTG GAC TGC AAA GTG       192
Ser Ser Gly Gly Gly Arg Gly Ser Ser Arg Arg Leu Asp Cys Lys Val
        50                  55                  60

ATC CGT CTG GCT GAG TGT GTG AGT GTG GCC CCC GTC ACC GTG GAG ACC       240
Ile Arg Leu Ala Glu Cys Val Ser Val Ala Pro Val Thr Val Glu Thr
 65                  70                  75                  80

CCC CCT GAG CCC GGC GCC ACT GCC TTC CGC CTG GAC ACT GCT CAG CGC       288
Pro Pro Glu Pro Gly Ala Thr Ala Phe Arg Leu Asp Thr Ala Gln Arg
                85                  90                  95

TCG CAC CTG CTG GCG GCC GAC GCG CCG TCC AGT GCA GCC TGG GTG CAG       336
Ser His Leu Leu Ala Ala Asp Ala Pro Ser Ser Ala Ala Trp Val Gln
```

-continued

| | | |
|---|---|---|
| ACG CTG TGC CGA AAC GCC TTT CCG AAA GGC AGC TGG ACT CTG GCG CCT<br>Thr Leu Cys Arg Asn Ala Phe Pro Lys Gly Ser Trp Thr Leu Ala Pro<br>115 120 125 | | 384 |
| ACC GAT AAC CCA CCT AAG CTT TCT GCC CTG GAG ATG CTG GAG AAC TCC<br>Thr Asp Asn Pro Pro Lys Leu Ser Ala Leu Glu Met Leu Glu Asn Ser<br>130 135 140 | | 432 |
| TTG TAC AGC CCT ACC TGG GAA GGA TCC CAA TTC TGG GTA ACG GTG CAG<br>Leu Tyr Ser Pro Thr Trp Glu Gly Ser Gln Phe Trp Val Thr Val Gln<br>145 150 155 160 | | 480 |
| AGG ACT GAG GCC GCC GAG CGC TGT GGC CTG CAT GGC TCC TAC GTG CTG<br>Arg Thr Glu Ala Ala Glu Arg Cys Gly Leu His Gly Ser Tyr Val Leu<br>165 170 175 | | 528 |
| AGG GTG GAG GCT GAA AGG CTG ACT CTC CTG ACC GTG GGG GCC CAG AGT<br>Arg Val Glu Ala Glu Arg Leu Thr Leu Leu Thr Val Gly Ala Gln Ser<br>180 185 190 | | 576 |
| CAG ATA CTG GAG CCA CTC CTG TCC TGG CCC TAC ACT CTG TTG CGT CGC<br>Gln Ile Leu Glu Pro Leu Leu Ser Trp Pro Tyr Thr Leu Leu Arg Arg<br>195 200 205 | | 624 |
| TAT GGC CGG GAC AAG GTC ATG TTC TCT TTC GAG GCC GGC CGC CGC TGC<br>Tyr Gly Arg Asp Lys Val Met Phe Ser Phe Glu Ala Gly Arg Arg Cys<br>210 215 220 | | 672 |
| CCC TCA GGC CCT GGA ACC TTC ACC TTC CAG ACG GCA CAG GGA AAT GAC<br>Pro Ser Gly Pro Gly Thr Phe Thr Phe Gln Thr Ala Gln Gly Asn Asp<br>225 230 235 240 | | 720 |
| ATC TTC CAG GCA GTT GAG ACT GCC ATC CAC CGG CAG AAG GCC CAG GGA<br>Ile Phe Gln Ala Val Glu Thr Ala Ile His Arg Gln Lys Ala Gln Gly<br>245 250 255 | | 768 |
| AAG GCC GGA CAG GGG CAC GAT GTT CTC AGA GCT GAC TCC CAT GAA GGG<br>Lys Ala Gly Gln Gly His Asp Val Leu Arg Ala Asp Ser His Glu Gly<br>260 265 270 | | 816 |
| GAG GTG GCA GAG GGG AAG TTG CCT TCC CCA CCT GGC CCC CAA GAG CTC<br>Glu Val Ala Glu Gly Lys Leu Pro Ser Pro Pro Gly Pro Gln Glu Leu<br>275 280 285 | | 864 |
| CTC GAC AGT CCC CCA GCC CTG TAT GCT GAG CCC TTA GAC TCC CTG CGC<br>Leu Asp Ser Pro Pro Ala Leu Tyr Ala Glu Pro Leu Asp Ser Leu Arg<br>290 295 300 | | 912 |
| ATT GCT CCA TGC CCT TCC CAG GAC TCC CTA TAC TCA GAC CCC TTG GAC<br>Ile Ala Pro Cys Pro Ser Gln Asp Ser Leu Tyr Ser Asp Pro Leu Asp<br>305 310 315 320 | | 960 |
| AGC ACG TCT GCT CAG GCA GGA GAG GGA GTA CAA CGG AAG AAA CCT CTC<br>Ser Thr Ser Ala Gln Ala Gly Glu Gly Val Gln Arg Lys Lys Pro Leu<br>325 330 335 | | 1008 |
| TAT TGG GAC TTG TAT GAG CAT GCG CAG CAG CAG TTG CTG AAG GCC AAG<br>Tyr Trp Asp Leu Tyr Glu His Ala Gln Gln Gln Leu Leu Lys Ala Lys<br>340 345 350 | | 1056 |
| CTG ACA GAC CCC AAA GAG GAT CCC ATC TAT GAT GAA CCT GAG GGC CTG<br>Leu Thr Asp Pro Lys Glu Asp Pro Ile Tyr Asp Glu Pro Glu Gly Leu<br>355 360 365 | | 1104 |
| GCC CCA GTC CCT CCC CAG GGC CTT TAT GAT CTG CCT CGG GAG CCC AAG<br>Ala Pro Val Pro Pro Gln Gly Leu Tyr Asp Leu Pro Arg Glu Pro Lys<br>370 375 380 | | 1152 |
| GAT GCA TGG TGG TGC CAA GCT CGG GTG AAG GAG GAG GGC TAT GAG CTC<br>Asp Ala Trp Trp Cys Gln Ala Arg Val Lys Glu Glu Gly Tyr Glu Leu<br>385 390 395 400 | | 1200 |
| CCC TAC AAC CCT GCC ACT GAT GAC TAC GCT GTG CCA CCC CCT CGG AGC<br>Pro Tyr Asn Pro Ala Thr Asp Asp Tyr Ala Val Pro Pro Pro Arg Ser<br>405 410 415 | | 1248 |
| ACA AAG CCC CTC CTT GCT CCC AAG CCC CAG GGC CCA GCC TTC CCT GAA | | 1296 |

```
Thr Lys Pro Leu Leu Ala Pro Lys Pro Gln Gly Pro Ala Phe Pro Glu
            420                 425                 430

CCT GGT ACT GCA ACT GGC AGT GGC ATC AAA AGC CAC AAC TCA GCC CTG          1344
Pro Gly Thr Ala Thr Gly Ser Gly Ile Lys Ser His Asn Ser Ala Leu
                435                 440                 445

TAC AGC CAG GTC CAG AAG AGC GGG GCC TCA GGG AGC TGG GAC TGT GGG          1392
Tyr Ser Gln Val Gln Lys Ser Gly Ala Ser Gly Ser Trp Asp Cys Gly
    450                 455                 460

CTC TCT AGA GTA GGG ACT GAC AAG ACT GGG GTC AAG TCA GAG GGC TCT          1440
Leu Ser Arg Val Gly Thr Asp Lys Thr Gly Val Lys Ser Glu Gly Ser
465                 470                 475                 480

ACC TGA                                                                   1446
Thr (2) INFORMATION FOR SEQ ID NO:2:

(i) SEQUENCE CHARACTERISTICS:
        (A) LENGTH: 481 amino acids
        (B) TYPE: amino acid
        (D) TOPOLOGY: linear (ii) MOLECULE TYPE: protein (xi) SEQUENCE DESCRIPTION: SEQ ID NO:2:

Met Asp Gly Ala Val Met Glu Gly Pro Leu Phe Leu Gln Ser Gln Arg
 1               5                  10                  15

Phe Gly Thr Lys Arg Trp Arg Lys Thr Trp Ala Val Leu Tyr Pro Ala
            20                  25                  30

Ser Pro His Gly Val Ala Arg Leu Glu Phe Phe Asp His Lys Gly Ser
        35                  40                  45

Ser Ser Gly Gly Gly Arg Gly Ser Ser Arg Arg Leu Asp Cys Lys Val
    50                  55                  60

Ile Arg Leu Ala Glu Cys Val Ser Val Ala Pro Val Thr Val Glu Thr
65                  70                  75                  80

Pro Pro Glu Pro Gly Ala Thr Ala Phe Arg Leu Asp Thr Ala Gln Arg
                85                  90                  95

Ser His Leu Leu Ala Ala Asp Ala Pro Ser Ser Ala Ala Trp Val Gln
            100                 105                 110

Thr Leu Cys Arg Asn Ala Phe Pro Lys Gly Ser Trp Thr Leu Ala Pro
        115                 120                 125

Thr Asp Asn Pro Pro Lys Leu Ser Ala Leu Glu Met Leu Glu Asn Ser
    130                 135                 140

Leu Tyr Ser Pro Thr Trp Glu Gly Ser Gln Phe Trp Val Thr Val Gln
145                 150                 155                 160

Arg Thr Glu Ala Ala Glu Arg Cys Gly Leu His Gly Ser Tyr Val Leu
                165                 170                 175

Arg Val Glu Ala Glu Arg Leu Thr Leu Leu Thr Val Gly Ala Gln Ser
            180                 185                 190

Gln Ile Leu Glu Pro Leu Leu Ser Trp Pro Tyr Thr Leu Leu Arg Arg
        195                 200                 205

Tyr Gly Arg Asp Lys Val Met Phe Ser Phe Glu Ala Gly Arg Arg Cys
    210                 215                 220

Pro Ser Gly Pro Gly Thr Phe Thr Phe Gln Thr Ala Gln Gly Asn Asp
225                 230                 235                 240

Ile Phe Gln Ala Val Glu Thr Ala Ile His Arg Gln Lys Ala Gln Gly
                245                 250                 255

Lys Ala Gly Gln Gly His Asp Val Leu Arg Ala Asp Ser His Glu Gly
```

```
                260                 265                 270
Glu Val Ala Glu Gly Lys Leu Pro Ser Pro Gly Pro Gln Glu Leu
                275                 280                 285

Leu Asp Ser Pro Pro Ala Leu Tyr Ala Glu Pro Leu Asp Ser Leu Arg
        290                 295                 300

Ile Ala Pro Cys Pro Ser Gln Asp Ser Leu Tyr Ser Asp Pro Leu Asp
305                 310                 315                 320

Ser Thr Ser Ala Gln Ala Gly Glu Gly Val Gln Arg Lys Lys Pro Leu
                325                 330                 335

Tyr Trp Asp Leu Tyr Glu His Ala Gln Gln Leu Leu Lys Ala Lys
                340                 345                 350

Leu Thr Asp Pro Lys Glu Asp Pro Ile Tyr Asp Glu Pro Glu Gly Leu
        355                 360                 365

Ala Pro Val Pro Pro Gln Gly Leu Tyr Asp Leu Pro Arg Glu Pro Lys
        370                 375                 380

Asp Ala Trp Trp Cys Gln Ala Arg Val Lys Glu Gly Tyr Glu Leu
385                 390                 395                 400

Pro Tyr Asn Pro Ala Thr Asp Asp Tyr Ala Val Pro Pro Pro Arg Ser
                405                 410                 415

Thr Lys Pro Leu Leu Ala Pro Lys Pro Gln Gly Pro Ala Phe Pro Glu
        420                 425                 430

Pro Gly Thr Ala Thr Gly Ser Gly Ile Lys Ser His Asn Ser Ala Leu
        435                 440                 445

Tyr Ser Gln Val Gln Lys Ser Gly Ala Ser Gly Ser Trp Asp Cys Gly
        450                 455                 460

Leu Ser Arg Val Gly Thr Asp Lys Thr Gly Val Lys Ser Glu Gly Ser
465                 470                 475                 480

Thr (2) INFORMATION FOR SEQ ID NO:3:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:3:

Gln Gly Xaa Asp Val Leu Arg Ala Asp
1               5

(2) INFORMATION FOR SEQ ID NO:4:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:4:

Pro Gln Gly Pro Ala Phe Pro Glu Pro Gly Thr Ala Thr Gly Ser
1               5                   10                  15

(2) INFORMATION FOR SEQ ID NO:5:

(i) SEQUENCE CHARACTERISTICS:
```

(A) LENGTH: 10 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:5:

Ser Xaa Thr Leu Ala Pro Thr Asp Asn Asn
1               5                   10

(2) INFORMATION FOR SEQ ID NO:6:

(i) SEQUENCE CHARACTERISTICS:
        (A) LENGTH: 17 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:6:

Gly Gln Gly His Asp Val Leu Arg Ala Asp Ser His Glu Gly Xaa Val
1               5                   10                  15

Ala (2) INFORMATION FOR SEQ ID NO:7:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:7:

Trp Ala Val Leu Tyr Pro Ala Ser Pro His Gly Val Ala Arg Leu Glu
1               5                   10                  15

Phe Phe Asp His Lys
            20

(2) INFORMATION FOR SEQ ID NO:8:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:8:

Pro Leu Tyr Xaa Asp Leu Tyr Glu His Ala Gln Gln Leu Leu Lys
1               5                   10                  15

(2) INFORMATION FOR SEQ ID NO:9:

(i) SEQUENCE CHARACTERISTICS:
        (A) LENGTH: 38 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:9:

Met Phe Ser Phe Glu Ala Gly Arg Arg Xaa Pro Ser Gly Pro Gly Thr

```
  1               5                  10                 15
Phe Thr Phe Gln Thr Ala Gln Gly Asn Asp Ile Phe Gln Ala Val Glu
         20                 25                 30
Thr Ala Ile Xaa Arg Gln
         35
```

(2) INFORMATION FOR SEQ ID NO:10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(ix) FEATURE:
        (A) NAME/KEY: modified_base
        (B) LOCATION: 6
        (D) OTHER INFORMATION: /mod_base= i (ix) FEATURE:
        (A) NAME/KEY: modified_base
        (B) LOCATION: 9
        (D) OTHER INFORMATION: /mod_base= i (ix) FEATURE:
        (A) NAME/KEY: modified_base
        (B) LOCATION: 13
        (D) OTHER INFORMATION: /mod_base= i (xi) SEQUENCE DESCRIPTION: SEQ ID NO:10:

TGGGCNGTNT CTNTATCCC                                                   19

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(ix) FEATURE:
        (A) NAME/KEY: modified_base
        (B) LOCATION: 3
        (D) OTHER INFORMATION: /mod_base= i (ix) FEATURE:
        (A) NAME/KEY: modified_base
        (B) LOCATION: 7
        (D) OTHER INFORMATION: /mod_base= i (ix) FEATURE:
        (A) NAME/KEY: modified_base
        (B) LOCATION: 18
        (D) OTHER INFORMATION: /mod_base= i (ix) FEATURE:
        (A) NAME/KEY: modified_base
        (B) LOCATION: 25
        (D) OTHER INFORMATION: /mod_base= i (xi) SEQUENCE DESCRIPTION: SEQ ID NO:11:

GTNTCTNTAT CCCTAGCNTA CGCCNCATGG                                30

(2) INFORMATION FOR SEQ ID NO:12:

(i) SEQUENCE CHARACTERISTICS:

```
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(ix) FEATURE:
        (A) NAME/KEY: modified_base
        (B) LOCATION: 3
        (D) OTHER INFORMATION: /mod_base= i (ix) FEATURE:
        (A) NAME/KEY: modified_base
        (B) LOCATION: 7
        (D) OTHER INFORMATION: /mod_base= i (ix) FEATURE:
        (A) NAME/KEY: modified_base
        (B) LOCATION: 11
        (D) OTHER INFORMATION: /mod_base= i (xi) SEQUENCE DESCRIPTION: SEQ ID NO:12:

TTNAGANAGA NAGATCTCTG TCTGTCTGAG CTGC                              34

(2) INFORMATION FOR SEQ ID NO:13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(ix) FEATURE:
        (A) NAME/KEY: modified_base
        (B) LOCATION: 13
        (D) OTHER INFORMATION: /mod_base= i (xi) SEQUENCE DESCRIPTION: SEQ ID NO:13:

TCTGTCTGTC TGNGCATGTC TCAGTA                                       26

(2) INFORMATION FOR SEQ ID NO:14:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(ix) FEATURE:
        (A) NAME/KEY: modified_base
        (B) LOCATION: 6
        (D) OTHER INFORMATION: /mod_base= i (ix) FEATURE:
        (A) NAME/KEY: modified_base
        (B) LOCATION: 9
        (D) OTHER INFORMATION: /mod_base= i (ix) FEATURE:
        (A) NAME/KEY: modified_base
        (B) LOCATION: 12
        (D) OTHER INFORMATION: /mod_base= i (ix) FEATURE:
        (A) NAME/KEY: modified_base
        (B) LOCATION: 16
        (D) OTHER INFORMATION: /mod_base= i
```

```
    (ix) FEATURE:
          (A) NAME/KEY: modified_base
          (B) LOCATION: 20
          (D) OTHER INFORMATION: /mod_base= i (xi) SEQUENCE DESCRIPTION: SEQ ID NO:14:

CATGGNGTNG CNACGNTCTN GAAGTT                                                  26

(2) INFORMATION FOR SEQ ID NO:15:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "primer"

(ix) FEATURE:
         (A) NAME/KEY: modified_base
         (B) LOCATION: 5
         (D) OTHER INFORMATION: /mod_base= i (ix) FEATURE:
         (A) NAME/KEY: modified_base
         (B) LOCATION: 19
         (D) OTHER INFORMATION: /mod_base= i (xi) SEQUENCE DESCRIPTION: SEQ ID NO:15:

TCTGNGCATG TCTCAGTANA GAAGTC                                                  26

(2) INFORMATION FOR SEQ ID NO:16:

(i) SEQUENCE CHARACTERISTICS:
         (A) LENGTH: 16 amino acids
         (B) TYPE: amino acid
         (C) STRANDEDNESS: Not Relevant
         (D) TOPOLOGY: linear (ii) MOLECULE TYPE: peptide (xi) SEQUENCE DESCRIPTION: SEQ ID NO:16:

Pro Gln Gly Pro Ala Phe Pro Glu Pro Gly Thr Ala Thr Gly Ser Cys
1               5                   10                  15

(2) INFORMATION FOR SEQ ID NO:17:

(i) SEQUENCE CHARACTERISTICS:
         (A) LENGTH: 8 amino acids
         (B) TYPE: amino acid
         (C) STRANDEDNESS: Not Relevant
         (D) TOPOLOGY: linear (ii) MOLECULE TYPE: peptide (xi) SEQUENCE DESCRIPTION: SEQ ID NO:17:

Asn Val Leu Tyr Ala Ala Pro Phe
1               5

(2) INFORMATION FOR SEQ ID NO:18:

(i) SEQUENCE CHARACTERISTICS:
         (A) LENGTH: 5 amino acids
         (B) TYPE: amino acid
         (C) STRANDEDNESS: Not Relevant
         (D) TOPOLOGY: linear (ii) MOLECULE TYPE: peptide
```

```
       (xi) SEQUENCE DESCRIPTION: SEQ ID NO:18:

Leu Tyr Ala Glu Pro
1               5

(2) INFORMATION FOR SEQ ID NO:19:

(i) SEQUENCE CHARACTERISTICS:
          (A) LENGTH: 6 amino acids
          (B) TYPE: amino acid
          (C) STRANDEDNESS: Not Relevant
          (D) TOPOLOGY: linear (ii) MOLECULE TYPE: peptide (xi) SEQUENCE DESCRIPTION: SEQ ID NO:19:

Asn Leu Tyr Xaa Xaa Pro
1               5

(2) INFORMATION FOR SEQ ID NO:20:

(i) SEQUENCE CHARACTERISTICS:
          (A) LENGTH: 8 amino acids
          (B) TYPE: amino acid
          (C) STRANDEDNESS: Not Relevant
          (D) TOPOLOGY: linear (ii) MOLECULE TYPE: peptide (xi) SEQUENCE DESCRIPTION: SEQ ID NO:20:

Ser Ala Leu Tyr Ser Gln Val Gln
1               5
```